United States Patent [19]

Cramer et al.

[11] Patent Number: 5,478,924

[45] Date of Patent: Dec. 26, 1995

[54] DISPLACEMENT CHROMATOGRAPHY OF PROTEINS USING LOW MOLECULAR WEIGHT DISPLACERS

[76] Inventors: Steven M. Cramer, 783 Trottingham Dr., Schenectady, N.Y. 12309; James A. Moore, 3 Audrey La., R.D. #4; Amitava Kundu, 77 Eagle St. (Apt #2), both of Troy, N.Y. 12180; Yufei Li, Institute of Chemistry, Academia Sinica, Beijing, China; Guhan Jayaraman, A-14 4 57 Burkitt Road, T. Nagar, Madras, Ind., 600017

[21] Appl. No.: 197,146

[22] Filed: Feb. 16, 1994

[51] Int. Cl.[6] .............................. C07K 1/14; C07K 1/16; C07K 1/18; C07C 211/62

[52] U.S. Cl. .................. 530/416; 530/412; 530/415; 530/344; 564/292; 564/295

[58] Field of Search .............................. 530/416, 415, 530/412, 344; 564/292, 294, 295

[56] References Cited

U.S. PATENT DOCUMENTS

| | | | |
|---|---|---|---|
| 2,946,757 | 7/1960 | Butler et al. | 521/38 |
| 3,651,231 | 3/1972 | Eppstein et al. | 530/399 |
| 5,028,696 | 7/1991 | Torres et al. | 530/387 |
| 5,043,423 | 8/1991 | Viscomi et al. | 530/344 |
| 5,156,835 | 10/1992 | Nabi et al. | 424/52 |

OTHER PUBLICATIONS

Cramer and Brooks "Ion–Exchange Displacement Chromatography of Proteins" *ACS Symposium Series*, 27–52 (1993).
Frenz et al. "Investigation of Operating Parameters in High–Performance Displacement Chromatography" *J. Chrom.*, 330, 1–17 (1985).
Valko et al. "Displacement Chromatography of Oligomycins" *J. Chrom.*, 386, 345–351 (1987).
Viscomi et al. "High–Performance Displacement Chromatography of Melanotropins and Their Derivatives" *J. Chrom.*, 440, 157–164 (1988).
Viscomi et al. "Preparative Purification of *Plasmodium falciparum* Circumsporozoite Protein . . . " *J. Chrom.*, 482, 99–106 (1989).
Vigh et al. "Displacement Chromatography On Cyclodextrin–Silicas" *J. Chrom.*, 484, 237–250 (1989).
Carcinali et al. "Scaling–Up Procedure From the Range of Milligrams to Grams For The Purification of Amino Acid . . . " *J. Chrom.*, 499 37–45 (1990).
Torres and Peterson "Purification of complex protein mixtures by ion–exchange . . . " *J. Chrom.*, 604, 39–46 (1992).
Kalghatgi et al. "Rapid displacement chromatography of melittin on micropellicular . . . " *J. Chrom.*, 604, 47–53 (1992).
Frenz et al. "Characterization of a Tryptic Digest By High–Performance . . . " *J. Chrom.*, 557, 289–305 (1991).
Viscomi et al. "Large–Scale Purification of the Synthetic Peptide Fragment . . . " *J. Chrom.*, 549, 175–184 (1991).
Ghose and Mattiasson "Evaluation of displacement chromatography for the recovery of lactate . . . " *J. Chrom.*, 547, 145–153 (1991).

(List continued on next page.)

*Primary Examiner*—Michael G. Wityshyn
*Assistant Examiner*—Nancy J. Degen
*Attorney, Agent, or Firm*—Heslin & Rothenberg

[57] ABSTRACT

A method for the purification of proteins by displacement chromatography on ion exchange media using low molecular weight displacers is disclosed. Several classes of low molecular weight, charged species are exemplified, including aminoacids, peptides, antibiotics and dendrimeric polymers. Novel compounds useful as displacers are dendrimers of formula $$X^{-+}(R^1)_3N{+}CH_2{\xrightarrow{}_n}O\diagup\diagdown\begin{matrix}O{+}CH_2{\xrightarrow{}_n}N(R^1)_3{}^+X^-\\O{+}CH_2{\xrightarrow{}_n}N(R^1)_3{}^+X^-\\O{+}CH_2{\xrightarrow{}_n}N(R^1)_3{}^+X^-\end{matrix}$$

wherein $R^1$ is lower alkyl, n is 2 to 6, and X is a common counter anion and similar dendritic polymers based thereon.

14 Claims, 8 Drawing Sheets

OTHER PUBLICATIONS

Verbalis "Heterogeneity of human pituitary neurophysins by ampholyte . . . " *J. Chrom.*, 254, 309–314 (1983).

Liao et al. "High Performance Displacement Chromatography of Proteins: Separation of . . . " *Chromatographia*, 24, 881–885 (1987).

Jen and Pinto "Use of the sodium salt of poly(vinylsulfonic acid) as a low–molecular–weight displacer . . . " *J. Chromatogr.*, 519, 87–98 (1990).

Jen and Pinto "Dextran Sulfate as a Displacer for the Displacement Chromotography of . . . " *J. Chromatogr.*, 29, 478–484 (1991).

Gerstner and Cramer "Cation–Exchange Displacement Chromatography of Proteins with . . . " *Biotechnol. Prog.*, 8, 540–545 (1992).

Jen and Pinto "Influence of displacer properties of displacement chromatography of . . . " *Reactive Polymers*, 19, 145–161 (1993).

Jayaraman et al. "Ion–exchange displacement chromatography of proteins . . . " *J. Chromtogr.*, 630, 53–68 (1993).

Chemical Abstracts vol. 105: 154826 (1986).

Newlcome et al. "Cascade Molecules: A New Approach to Micellses" J. Org. Chem. 50 2003–2004 1985.

Eckstein et al. "Synthese Vernetzter Lysin–und Lysinpeptidgele" Makromol Chem 181 2471–2480 1980. Abstract.

Chromtography Ed. Hytmann pp. A30–A33 1983.

DISPLACEMENT CHROMATOGRAPHY OF PROTEINS USING LOW MOLECULAR WEIGHT DISPLACERS

STATEMENT AS TO RIGHTS UNDER FEDERALLY SPONSORED RESEARCH

This invention was made with support from the National Science Foundation Grant No. BCS-9112481. The United States government may have certain rights in the invention.

FIELD OF THE INVENTION

This invention relates to the displacement chromatography of proteins using low molecular weight displacers and to a novel class of dendritic polymer based polyelectrolytes useful for chromatography of proteins.

BACKGROUND OF THE INVENTION

The displacement mode of chromatography was first recognized in 1906 by Tswett, who noted that sample displacement occurred under conditions of overloaded elution chromatography. In 1943, Tiselius developed the classifications of frontal chromatography, elution chromatography, and displacement chromatography. Since that time most developments and applications, particularly those in analytical chromatography, have taken place in the area of elution chromatography, and indeed the term chromatography without further qualification usually refers to elution chromatography. Nonetheless, while the theory and practice of elution chromatography has dominated the literature for the past fifty years, the theory and practice of displacement chromatography has occupied a small niche in chromatographic science.

The two types of chromatography, elution and displacement, are readily distinguished both in theory and in practice. In elution chromatography, a solution of the sample to be purified (in the case of the present invention, a protein) is applied to a stationary phase, commonly in a column. The mobile phase is chosen such that the sample is neither irreversibly adsorbed nor totally unadsorbed, but rather binds reversibly. As the mobile phase is flowed over the stationary phase, an equilibrium is established between the mobile phase and the stationary phase whereby, depending upon the affinity for the stationary phase, the sample passes along the column at a speed which reflects its affinity relative to other components that may occur in the original sample. The differential migration process is outlined schematically FIG. 1, and a typical chromatogram is shown in FIG. 2. Of particular note in standard elution chromatography is the fact that the eluting solvent front, or zero column volume in isocratic elution, always precedes the sample off the column.

A modification and extension of isocratic elution chromatography is found in step gradient chromatography wherein a series of eluents of varying composition are passed over the stationary phase. In ion exchange chromatography, step changes in the mobile phase salt concentration and/or pH are employed to elute or desorb the proteins.

Displacement chromatography is fundamentally different from desorption chromatography (e.g., affinity chromatography, step gradient chromatography). The displacer, having an affinity higher than any of the feed components, competes effectively for the adsorption sites on the stationary phase. An important distinction between displacement and desorption is that the displacer front always remains behind the adjacent feed zones in the displacement train, while desorbents (e.g., salt, organic modifiers) move through the feed zones. The implications of this distinction are quite significant in that displacement chromatography can potentially concentrate and purify components from mixtures having low separation factors while in the case of desorption chromatography, relatively large separation factors are generally required to give satisfactory resolution.

In displacement chromatography the eluent, (i.e. the displacer) has a higher affinity for the stationary phase than does any of the components in the mixture to be separated. This is in contrast to elution chromatography, where the eluent usually has a lower affinity. The key operational feature which distinguishes displacement chromatography from elution or desorption chromatography is the use of a displacer molecule. In displacement chromatography, the column is first equilibrated with a carrier solvent under conditions in which the components to be separated all have a relatively high affinity for the stationary phase. A large volume of dilute feed mixture can be loaded onto the column and individual components will adsorb to the stationary phase. That is, they distribute from the feed solution onto the stationary phase, and remain there. If all the components are to be resolved by displacement, the carrier solvent emerges from the column containing no sample. The sample now resides on the stationary phase and the position of each component on the column is correlated with its relative affinity for the stationary phase. Conceptually, one can imagine each molecule of the component with the highest affinity for the stationary phase displacing a molecule of a component having a lower affinity at a site on the stationary phase so that the individual components will ultimately be arranged on the column in sequence from highest to lowest affinity.

It will sometimes be advantageous to allow some of the components to pass through the column with the carrier solvent; in this case only the retained feed components will be resolved by displacement chromatography.

Once the sample is loaded on the column, a displacer solution is introduced. The displacer solution comprises a displacer in a suitable solvent. The displacer is selected such that it has a higher affinity for the stationary phase than does any of the feed components. Assuming that the displacer and mobile phase are appropriately chosen, the product components exit the column as adjacent squarewave zones of highly concentrated pure material in the order of increasing affinity of absorption. This is shown schematically in FIG. 3. Following the zones of purified components, the displacer emerges from the column. A typical chromatogram from a displacement chromatography is shown in FIG. 4. It is readily distinguished from the chromatogram of elution chromatography shown in FIG. 2 by virtue of the fact that the displacer follows the sample and that the feed components exit the column as adjacent "square wave" zones of highly concentrated pure material. Finally, after the breakthrough of the displacer, the column is regenerated by desorbing the displacer from the stationary phase to allow the next cycle of operation.

Displacement chromatography has some particularly advantageous characteristics for process scale chromatography of biological macromolecules such as proteins. First, and probably most significantly, displacement chromatography can achieve product separation and concentration in a single step. By comparison, isocratic elution chromatography results in product dilution during separation. Second, since the displacement process operates in the nonlinear region of the equilibrium isotherm, high column loadings are possible. This allows much better column utilization than elution chromatography. Third, column development per se requires less solvent than a comparable elution process. Fourth, displacement chromatography can concentrate and purify components from mixtures having low separation factors, while relatively large separation factors are required for satisfactory resolution in desorption chromatography.

With all of these advantages, one might presume that displacement chromatography would be widely utilized. However, displacement chromatography, as it is traditionally known, has a number of drawbacks vis-à-vis elution chromatography for the purification of proteins The term "protein", as commonly understood in the art and as used herein, refers to polypeptides of 10 kDa molecular weight or more; according to this convention, polypeptides of molecular weight below 10 kDa are commonly referred to as oligopeptides. Two of the major problems are (1) regeneration of the column and (2) the presence of displacer in some of the purified fractions.

Since the displacement process uses a high affinity compound as the displacer, the time for regeneration and re-equilibration can be long compared to elution chromatography. Furthermore, relatively large amounts of solvent are often required during regeneration, effectively reducing any advantage over elution chromatography in solvent consumption.

The second problem, that of contamination by the displacer, has arisen because a common characteristic of displacers used in protein separations has been their relatively high molecular weight. Heretofore the art has taught the use of high molecular weight polyelectrolytes to displace proteins on the assumption that (as explained below) it is necessary to have a large polyelectrolyte in order to ensure a higher binding coefficient than the protein that is to be displaced. High molecular weight displacers exhibit both of the disadvantages enumerated above: they bind tightly to the stationary phase and therefore require heroic conditions for regenerating the column, and traces of the displacer that may contaminate the product fraction are difficult to remove.

Therefore, it would be advantageous to have a class of displacers that did not require extensive regeneration of the column and that could be readily removed from the product protein. There is one example in the art known to applicants of an attempt to use 2 kilodalton poly(vinylsulfonic acid) on polyethyleneimine-coated weak anion exchange resin for the separation of conalbumin from ovalbumin. The experiment appears to have been successful in that the two proteins were separated [See Jen and Pinto *Journal of Chromatography* 519, 87–98 (1990)]. However the separation appeared to have been effected by a mixed mechanism of elution and displacement chromatography, as discussed in a subsequent paper [see Jen and Pinto *Journal of Chromatographic Science* 29, 478–484 (1991)] in which the authors abandoned the poly(vinyl sulfate) displacers in favor of higher molecular weight dextran sulfate. In this second paper, Jen and Pinto demonstrate the superiority of the larger dextran sulfate over the smaller polyvinyl sulfate.

In a subsequent article, Jen and Pinto [*Reactive Polymers* 19, 145–161 (1993), p.147] provide a table of all displacers used for the displacement chromatography of proteins on ion exchange stationary phases. In their discussion of the results, they conclude, as before, that the 2 kDa polyvinyl sulfate partially displaces the second protein and elutes the first.

It has now been surprisingly found that several classes of charged species of very low molecular weight can function very efficiently as displacers for proteins in displacement chromatography.

SUMMARY OF THE INVENTION

In one aspect, the invention relates to a method for purifying a protein, or several proteins, comprising loading the protein in a suitable mobile phase onto an ion exchange stationary phase and displacing the protein from the stationary phase by displacement chromatography using a displacer of molecular weight less than 2000.

In one embodiment the stationary phase is a cation exchange resin and the displacer is a cationic species; in another embodiment the stationary phase is an anion exchange resin and the displacer is an anionic species. In various preferred embodiments the displacer is a poly(quaternary ammonium) salt, or the displacer is an aminoacid ester, N-acylaminoacid, peptide ester or N-acyl peptide, preferably a lower alkyl ester of lysine, lower alkyl ester of arginine, lower alkyl ester of $N^\alpha$-acylated lysine or lower alkyl ester of $N^\alpha$-acylated arginine. Lower alkyl refers to linear, branched or cyclic, saturated hydrocarbon residues of six or fewer carbons. The displacer may also be a cationic or anionic antibiotic, or a dendritic polymer. When the displacer is a dendritic polymer, a preferred displacer is

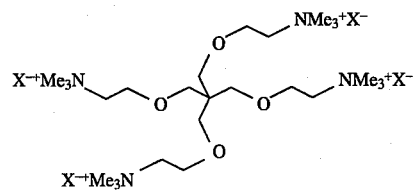

wherein $X^-$ is a counter anion, for example halogen, sulfate, sulfonate, perchlorate, acetate, phosphate or nitrate.

Generally, the displacer may be advantageously selected from electrolytes whose characteristic charge (ν) and equilibrium constant (K) are such that when a coordinate system representing log K on the ordinate and ν on the abscissa is created, a line constructed from a point A on the ordinate axis through a point defined by the K and the ν of the displacer has a greater slope than a corresponding line constructed from the same point A through a point defined by the K and the ν of the protein to be purified. The point A corresponds in value to the slope of the displacer operating line (Δ) in the system of interest. This will be explained in greater detail below.

In another aspect the invention relates to a method for purifying a protein comprising loading the protein in a suitable loading solvent onto an ion exchange stationary phase and displacing the protein from the stationary phase by displacement chromatography using a dendritic polyelectrolyte displacer. The stationary phase can be a cation exchange resin, in which case the polyelectrolyte will be a polycation, or the stationary phase can be an anion exchange resin, in which case the polyelectrolyte will be a polyanion. Preferably, the polyelectrolyte is a poly(quaternary ammonium) salt. Another preferred dendritic polymer is

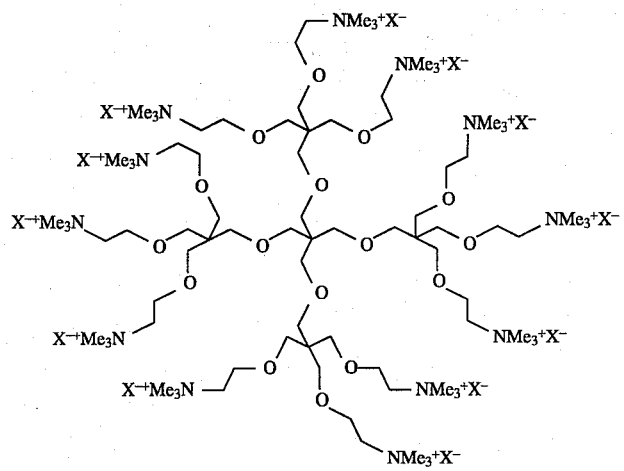

In another aspect, the invention relates to compounds of formula

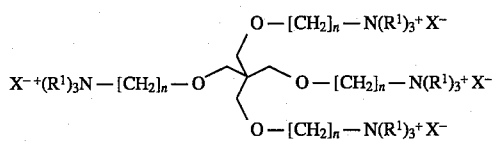

and

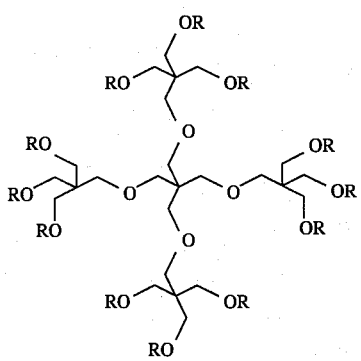

wherein R is —$(CH_2)_n$—$N(R^1)_3^+ X^-$, $R^1$ is lower alkyl n is 2 to 6, and X is as before. The compounds are useful as displacers in displacement chromatography.

DETAILED DESCRIPTION OF THE INVENTION INCLUDING PREFERRED EMBODIMENTS

Figure 1:
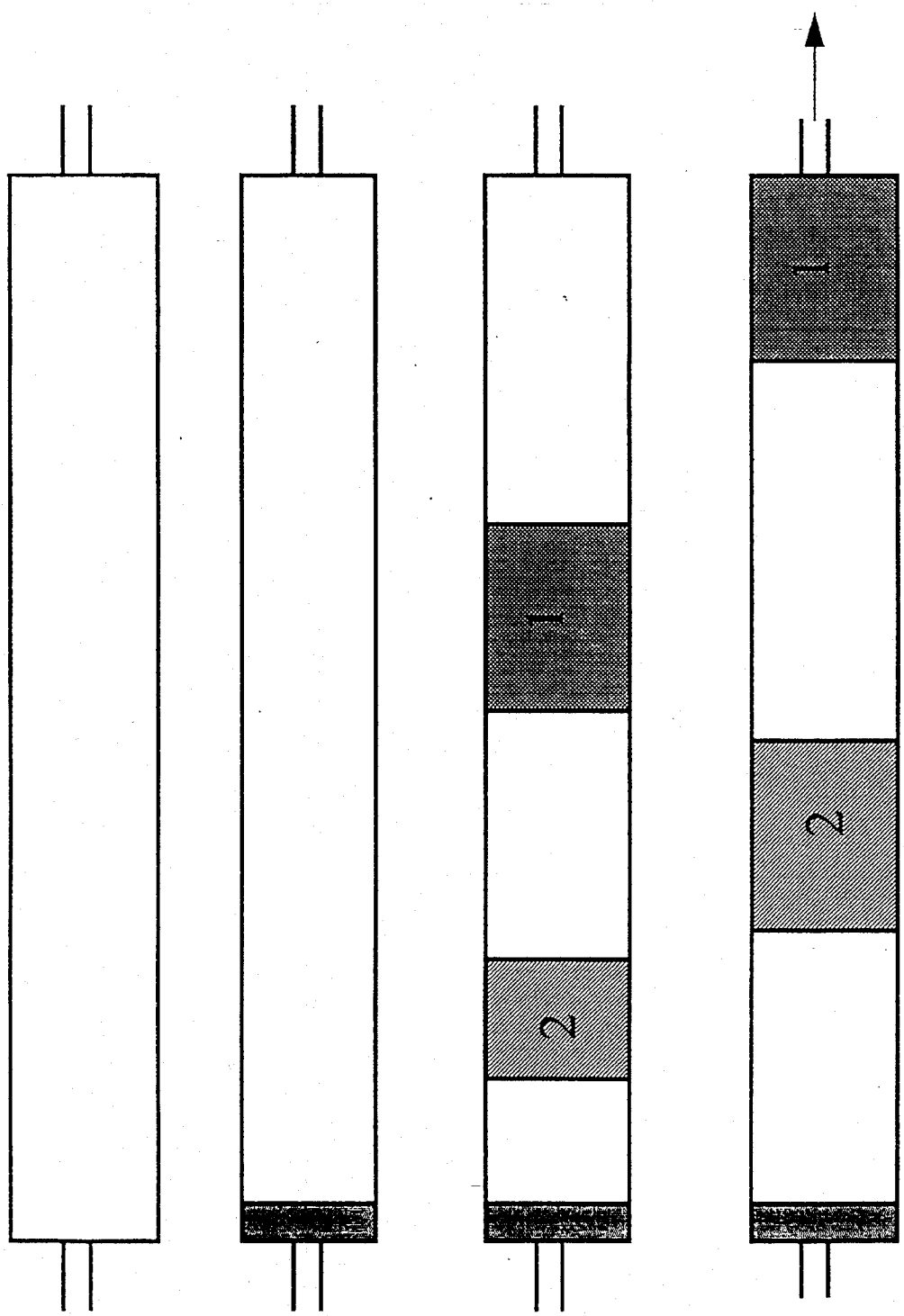
FIG. 1 is a schematic representation of a standard isocratic linear elution chromatography.
Figure 2:
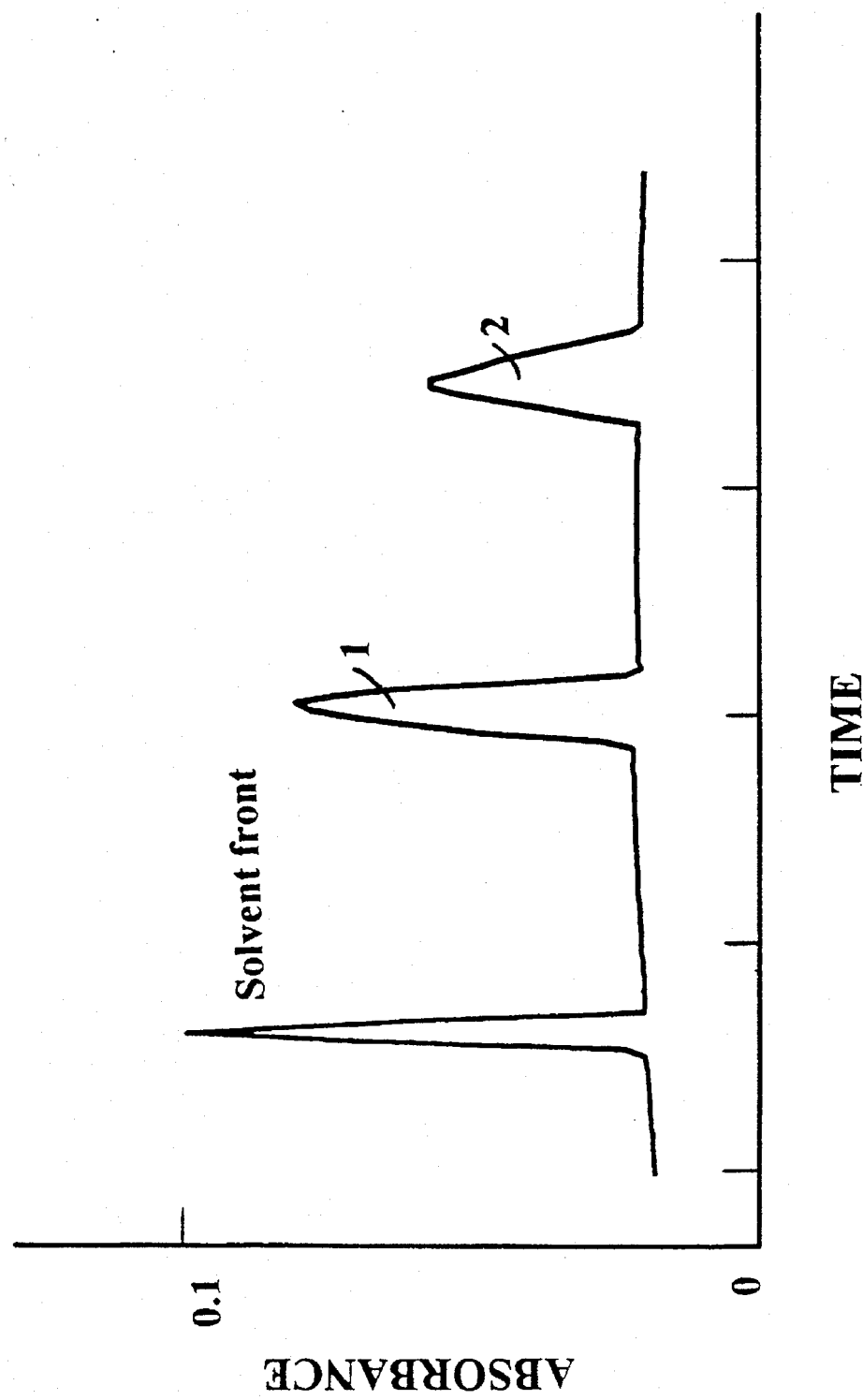
FIG. 2 is a typical chromatogram from elution chromatography.
Figure 3:
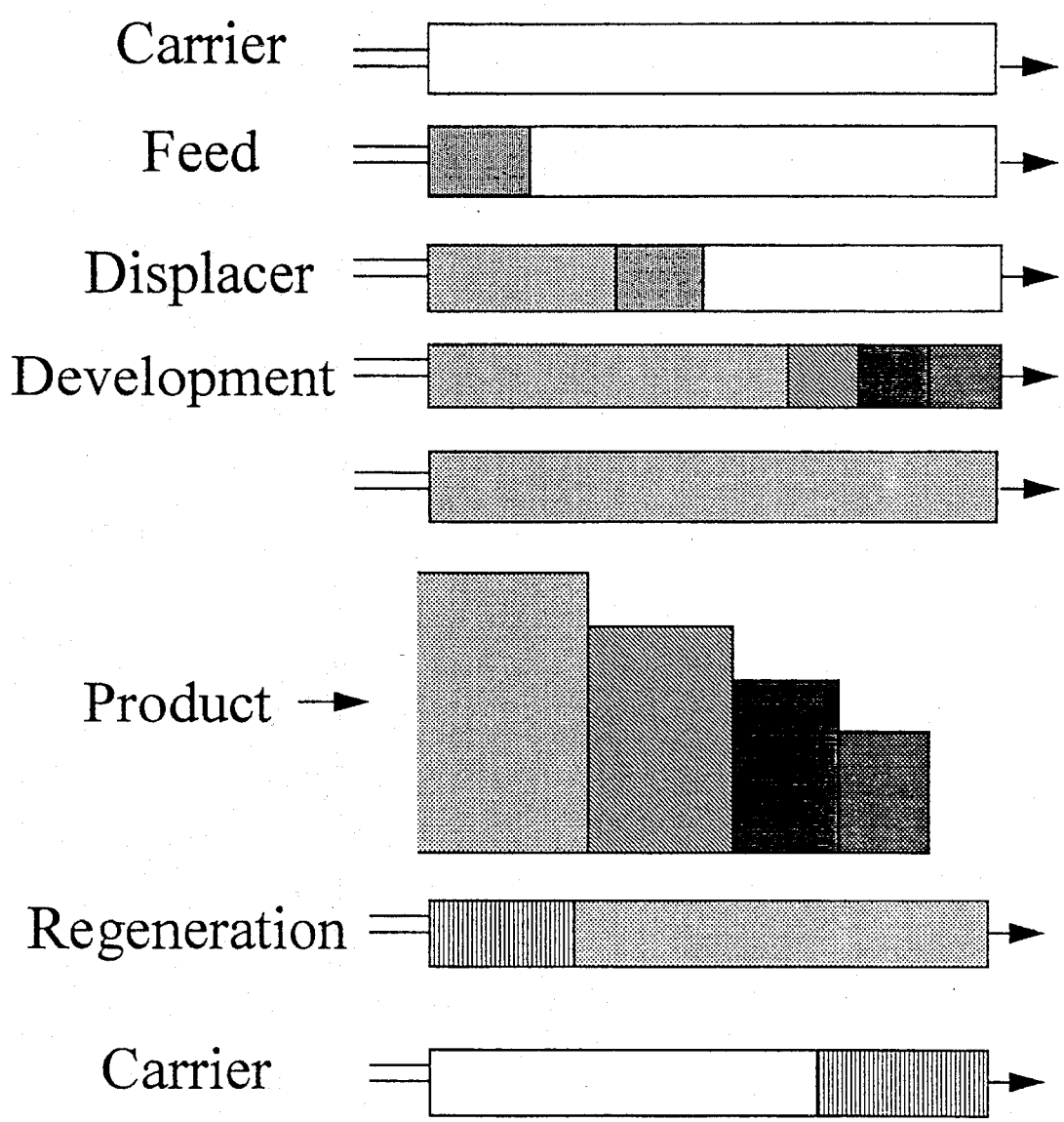
FIG. 3 is a schematic representation of displacement chromatography.
Figure 4:
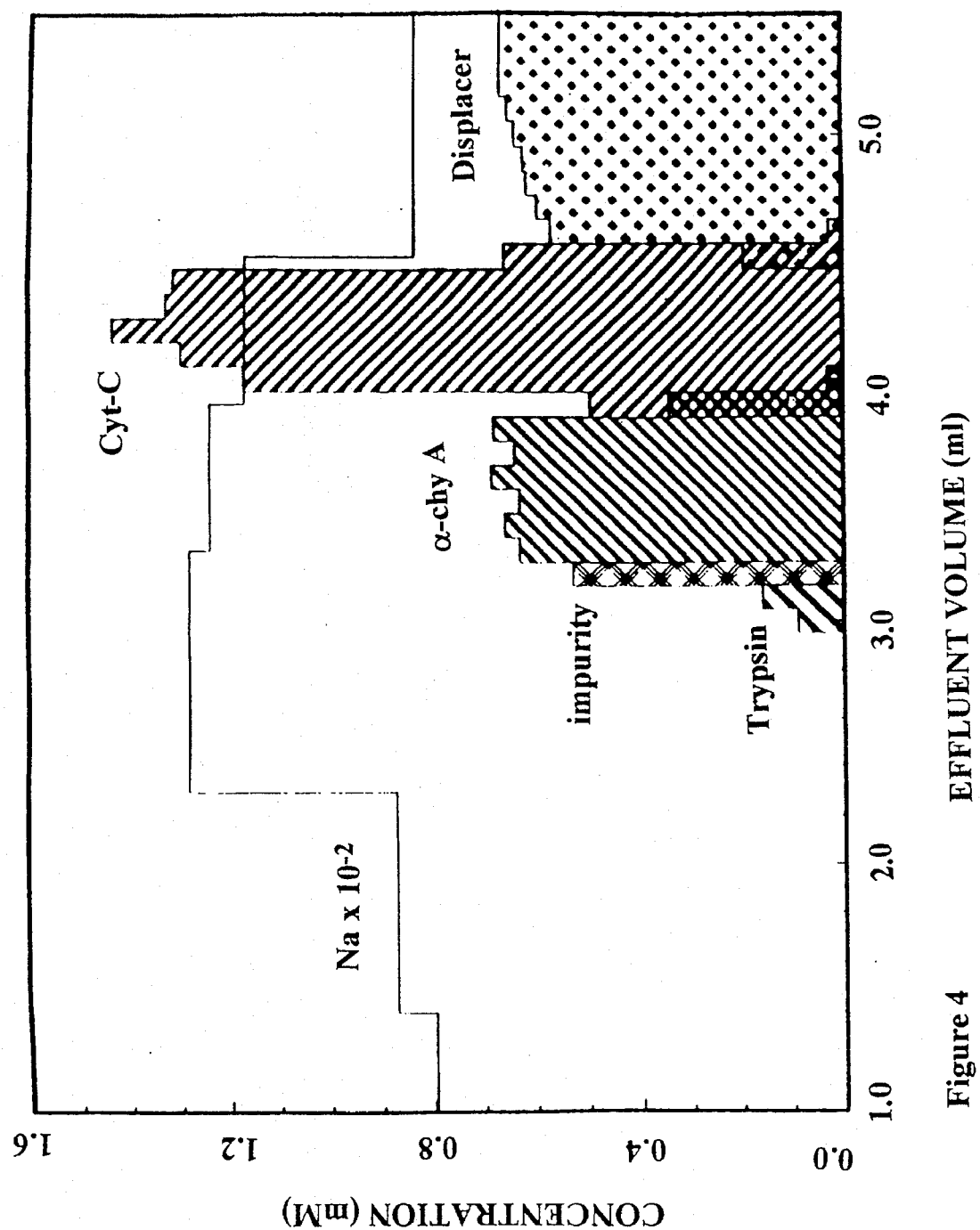
FIG. 4 is a typical chromatogram from displacement chromatography.

A better understanding of the surprising discovery that small molecules can be used effectively as displacers in the chromatography of proteins is gained by briefly considering an improved mathematical model for displacement chromatography. Although this hypothetical construct is useful to rationalize the phenomenon, it is not intended to limit the full breadth of the invention.

The steric mass action (SMA) ion exchange model developed by one of the inventors, unlike other models, explicitly accounts for steric effects in multicomponent protein equilibria and is able to predict complex behavior in ion exchange displacement systems. A macromolecular solute like a protein or a polyelectrolyte is presumed to have a multi-point attachment on an ion-exchange surface and the number of interactions between the absorbent surface and a single macromolecule is defined as the characteristic charge of the solute molecule. The characteristic charge of a solute is numerically equal to the number of salt counter-ions displaced by the solute from the ion-exchange surface upon adsorption. However, in addition to the =sites at which the polyelectrolyte actually interacts, a large solute macromolecule bound to an ion-exchange surface also sterically hinders the adsorption of macromolecules of similar size onto sites underneath and adjoining the bound solute molecule. The number of sterically hindered salt counter-ions on the surface (per adsorbed solute molecule), unavailable for exchange with other solute molecules in the fluid phase is defined as the steric factor of the adsorbed macromolecule. Earlier treatments of mass action ion exchange equilibria assumed that the binding of a macromolecule to an adsorbent surface only affects a number of adsorbent sites equal to its characteristic charge. In fact, the steric shielding of the stationary phase sites plays an important role in the non-linear adsorption behavior of macromolecules in ion-exchange systems.

The stoichiometric exchange of a solute molecule (protein or polyelectrolyte) and the exchangeable salt counter-ions can be represented by:

$$C_i + v_i \overline{Q}_s \rightleftharpoons Q_i + v_i C_s \qquad (1)$$

where C and Q are the mobile and stationary phase concentrations; $v_i$ is the characteristic charge of the solute, and subscripts i and s refer to the solute molecule and the salt counter-ion respectively. The overbar denotes bound salt counter-ions available for exchange with the solute macromolecule in solution. The equilibrium constant, $K_i$, for the solute adsorbed on the ion-exchange surface is given by:

$$K_i = \left(\frac{Q_i}{C_i}\right)\left(\frac{C_s}{\overline{Q_s}}\right)^{v_i} \quad (2)$$

The equilibrium constant is a measure of the affinity of the molecule. The electro-neutrality condition on the stationary phase is given by the following relation:

$$\Lambda = \overline{Q}_s + (v_i + \sigma_i)Q_i \quad (3)$$

where $\sigma_i$ is the steric factor of the displacer or protein.

Substituting equation 3 into equation 2 and rearranging yields the following equilibrium relation for a single protein or displacer:

$$C_i = \left(\frac{Q_i}{K_i}\right)\left(\frac{C_s}{\Lambda - (v_i + \sigma)Q_i}\right)^{v_i} \quad (4)$$

Thus, knowing the values of the mobile phase counter-ion concentration $C_s$, the column ion-bed capacity, $\Lambda$, and the model parameters for each component, one can easily generate a single component isotherm from the implicit equation (4). The required model parameters for each component are: characteristic charge, $v_i$, steric factor, $\sigma_i$, and equilibrium constant $K_i$. In order to employ this model for predicting displacement behavior, it is necessary to determine model parameters for the proteins and the displacers.

Ion-bed capacity, $\Lambda$, can be measured in-situ using frontal chromatographic techniques [see Gadam et al., *J. Chromatog.* 630, 37–52 (1993)].

For protein molecules exhibiting significant salt-sensitive retention behavior under low to moderate salt concentrations in the mobile phase, linear elution chromatography can be employed to determine two of the three SMA model parameters (viz., characteristic charge and equilibrium constant) using well established relationships for ion-exchange systems [see Kopaciewicz et al., *J. Chromatog.* 266, 3 (1983)]. Linear elution experiments are carried out at various mobile phase salt concentrations in order to determine the characteristic charge ($v_i$) and equilibrium constant ($K_i$) by the following equations:

$$\log k' = \log(\beta K_i \Lambda^{v_i}) - v_i \log C_s \quad (5)$$

where, for a log k' v log $C_s$ plot, slope=$-v_i$; and intercept=log $(\beta K_i \Lambda^{v_i})$.

Having determined the characteristic charges and equilibrium constants for the proteins, the remaining SMA parameter, viz. steric factor, $\sigma_i$, for the proteins is determined independently from a single non-linear frontal chromatographic experiment according to the expression:

$$\sigma_i = \frac{\beta}{C_f \Pi}\left(\Lambda - C_s\left(\frac{\Pi}{\beta K_i}\right)^{1/v_i}\right) - v_i \quad (6)$$

where, $$\Pi = \left(\frac{V_b}{V_o} - 1\right) \quad (7)$$

Many proteins exhibit significantly higher steric factors relative to their characteristic charge, which is not surprising in light of the conformational constraints in the protein molecules. Once the SMA parameters are obtained for a given protein, the model can then be used to generate adsorption isotherms at any salt concentration.

While the determination of the characteristic charge and equilibrium constant from linear elution data works well for moderately retained proteins, it is quite difficult to characterize high affinity displacers in this fashion. Frontal chromatography, on the other hand, is well suited for parameter estimations for these high affinity compounds. The characteristic charge of the displacer, $v_D$, can be determined from the induced salt gradient using the following expression:

$$v_D = \frac{n_i}{n_D} = \frac{\Delta C_s}{C_D} \quad (8)$$

wherein $n_i$ is the total amount of ions displaced, $n_D$ is the number of moles of displacer adsorbed on the stationary phaser $C_D$ is the mobile phase concentration of polyelectrolyte displacer and $\Delta C_s$ is the step increase in the mobile phase counter-ion concentration upon displacer adsorption.

At sufficiently low mobile phase salt concentration the displacer completely saturates the stationary phase material. Frontal experiments under these conditions can be employed to determine the steric factor, $\sigma_D$, from the following expression $$\sigma_D = \frac{\Lambda}{Q_D^{max}} - n_D \quad (9)$$

where $\Lambda$ is the ion bed capacity and $Q_D^{max}$ is the maximum stationary phase capacity of the polyelectrolyte displacer. Alternatively, the steric factor could be determined by measuring, for example, the sterically hindered sodium ions displaced by an ammonium front (analogous to bed-capacity measurement), $n_2$, as given by $$\sigma_D = \frac{n_2}{n_D} \quad (10)$$

The equilibrium constant for the ion-exchange process is defined by equation 2. Once the characteristic charge and steric factor are measured independently as described above, a frontal experiment is employed for the determination of the equilibrium constant $K_D$, This experiment is performed under elevated mobile phase salt conditions where the solute does not completely saturate the bed. The equilibrium constant is directly calculated from the breakthrough volume using the independently determined values of the characteristic charge ($v_D$) and steric factor ($\sigma_D$) by the expression $$K_D = \frac{1}{\frac{1}{\beta}\left(\frac{V_b}{V_o} - 1\right)}\left(\frac{C_s}{\Lambda - (v_D + \sigma_D)\frac{C_D}{\beta}\left(\frac{V_b}{V_o} - 1\right)}\right)^{v_D} \quad (11)$$

where $\beta$ is the column phase ratio and $C_S$ is the initial salt concentration in the carrier. Once the characteristic charge, steric factor and equilibrium constants are determined, the isotherms of the proteins and polyelectrolytes can be simulated using the SMA formalism described above.

According to the conventional wisdom based on results observed with derivatized polysaccharide displacers, a high molecular weight compound with a relatively high characteristic charge and a high steric factor to characteristic charge ratio is needed for protein displacement chromatography. There have been heretofore no clearly defined criteria for selecting or determining the efficacy of one displacer over another. Using the mathematical model described above, it is now possible to predict the elution order of the feed components as a function of the characteristic charge and equilibrium constant of each of the components, once the slope of the displacer operating line is known.

Figure 5:
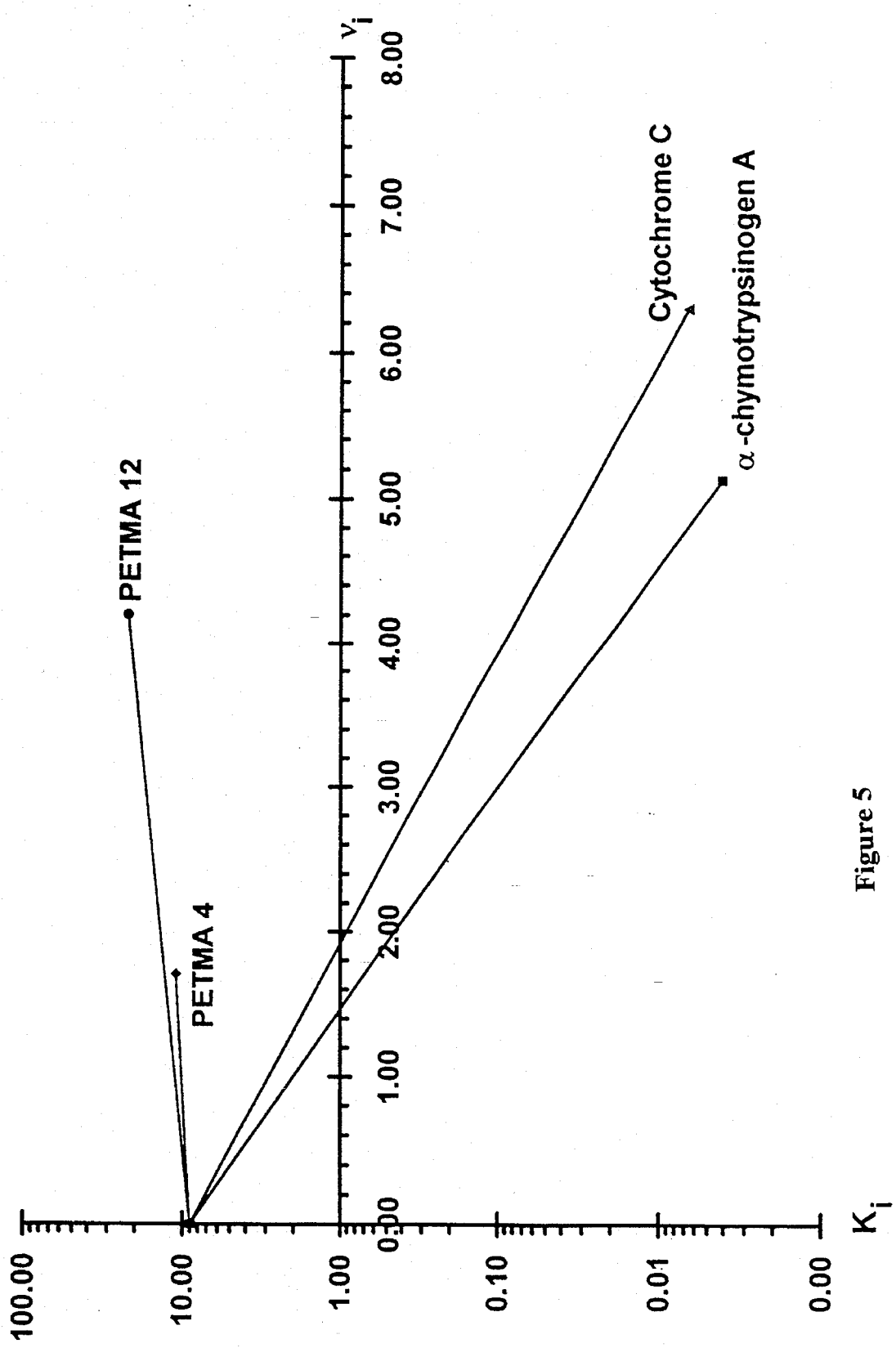
FIG. 5 is a plot of equilibrium constant (K) versus characteristic charge (v) for two proteins and two displacers of the invention.

The mathematical criterion for effective displacement chromatography can be reconstructed as a plot of log $K_i$ vs. $v_i$ (see FIG. 5). The elution order in the isotachic displacement train can be then graphically determined by constructing lines from the point on the ordinate axis corresponding to the slope of the displacer operating line, $\Delta$, $$\Delta = \frac{Q_d}{C_d} = K_{1_d}\left[\frac{\Lambda - (v_d + \sigma_d) Q_d}{(C_1)_d}\right] \quad (12)$$

through each of the points defined by the equilibrium parameters (characteristic charge and equilibrium constant) of the solutes. The order of elution of the feed components corresponds to the counterclockwise order (i.e. increasing slopes) of these "affinity" lines. In equation (12) $(C_1)_d$ is the concentration of salt that the displacer encounters (i.e. the carrier salt concentration), $Q_d$ is the concentration of the displacer on the stationary phase and $C_d$ is the concentration of displacer in the mobile phase.

Dendritic polymers (also known as starburst polymers) are three-dimensional, highly ordered oligomeric and polymeric compounds formed by reiterative reaction sequences starting from smaller molecules—"initiator cores" such as ammonia or pentaerythritol. With selected building blocks and propagation reactions, critical molecular design parameters such as size, shape, topology, flexibility and surface chemistry can be precisely controlled at the molecular level. The syntheses proceed via discrete stages referred to as generations. Dendrimers possess three distinguishing architectural features: (1) an initiator-core region, (2) interior zones containing cascading tiers of branch cells with radial connectivity to the initiator core, and (3) an exterior or surface region of terminal moieties attached to the outermost generation.

The synthesis of a zero (12), first (14) and second [(16) shown in scheme 2] generation pentaerythritol based dendrimer was carried out as described in detail later. The zero generation dendrimer is referred to for convenience as PETMA4, PentaErythrityl (TriMethylAmmonium)$_4$, the first generation as PETMA12, and the second as PETMA36.

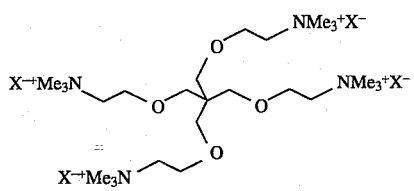

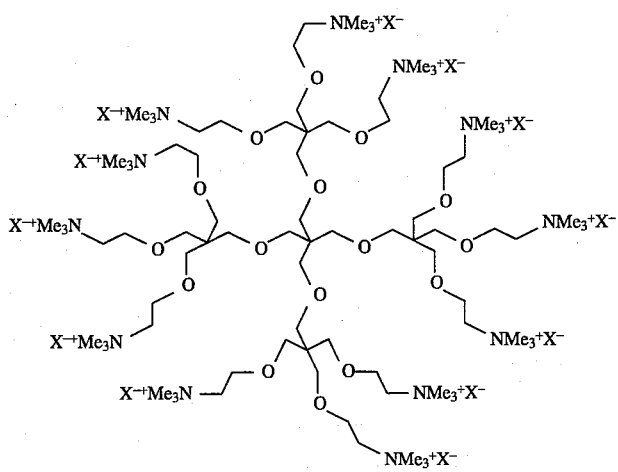

Although applicants do not wish to be bound by this hypothetical construct, it appears consistent with the discovery that small molecules can be effective displacers, because size is not the critical parameter. According to the theory, any molecule whose $K_i$ and $v_i$ places it counterclockwise on the affinity plot from the protein in question will function as an effective displacer for that protein.

Consistent with this prediction, a number of low molecular weight displacers have been tested and found effective for protein displacement.

The SMA model equilibrium parameters for the zero, first and second generation dendrimers were estimated in a 50×5 mm I.D. SCX column using frontal chromatographic techniques.

As can be seen from Table 1, approximately one-third of the total number of charges on each of the dendrimers bind to the surface. The first generation (PETMA12) and the second generation (PETMA36) dendrimers exhibited similar adsorption behavior, with similar values of $\sigma_D/v_D$ and $Q_D*v_D$ and marginal increases in $Q_D$ with decrease in salt concentration.

TABLE 1

AVERAGE VALUES OF SMA PARAMETERS FOR PENTAERYTHRITOL BASED DENDRIMERIC DISPLACERS

| Displacer (M.W.) | Salt (Na$^+$) Conc. (mM) | Solute Concen. C (mM) | Charac. Charge ($\nu_D$) | Steric Factor ($\sigma_D$) | ($\sigma_D/\nu_D$) | $Q_D$ (mM) | $Q_D*V_D$ (meq) |
|---|---|---|---|---|---|---|---|
| PETMA4 (480) | 20 | 15 | 1.5 | 2.6 | 1.73 | 140 | 210 |
| PETMA4 (480) | 50 | 21 | 1.6 | 1.5 | 0.94 | 183 | 293 |
| PETMA4 (480) | 50 | 4.18 | N.D. | N.D. | N.D. | 177 | N.D. |
| PETMA12 (1620) | 20 | 6.17 | 4.2 | 6.3 | 1.50 | 55.3 | 232 |
| PETMA12 (1620) | 75 | 6.17 | 4.2 | N.D. | N.D. | 51.5 | 216 |
| PETMA36 (5128) | 20 | 1.96 | 11 | 16.7 | 1.52 | 20.9 | 230 |
| PETMA36 (5128) | 50 | 1.96 | 10.5 | N.D. | N.D. | 18.3 | 192 |

As seen in Table 1, the second generation dendrimer PETMA36 has a relatively higher characteristic charge than the first generation dendrimer, but a similar $\sigma_i/\nu_i$ ratio. According to theory, PETMA36 should act as an efficient displacer, and that was indeed found to be the case. A two-protein displacement separation (α-chymotrypsinogen A and cytochrome C) using PETMA36 was carried out in a 100×5 mm cation exchange column. There was a reasonably good match of theory and experiment. The experiment was repeated using purified (diafiltered) first generation pentaerythritol PETMA12 as the displacer. These displacements indicate that decreasing the molecular weight and number of charged groups on the dendrimers appears to have little effect on their efficacy as displacers. Extending the prediction one level further, one would predict a zero generation dendrimer should also act as a protein displacer. This prediction runs counter to the conventional wisdom of using high-molecular weight polyelectrolytes with high characteristic charges as displacers of proteins in ion-exchange systems. (The zero generation dendrimer has a net charge of 4, a characteristic charge of 1.7 and a molecular weight of 480 Da.)

Figure 6:
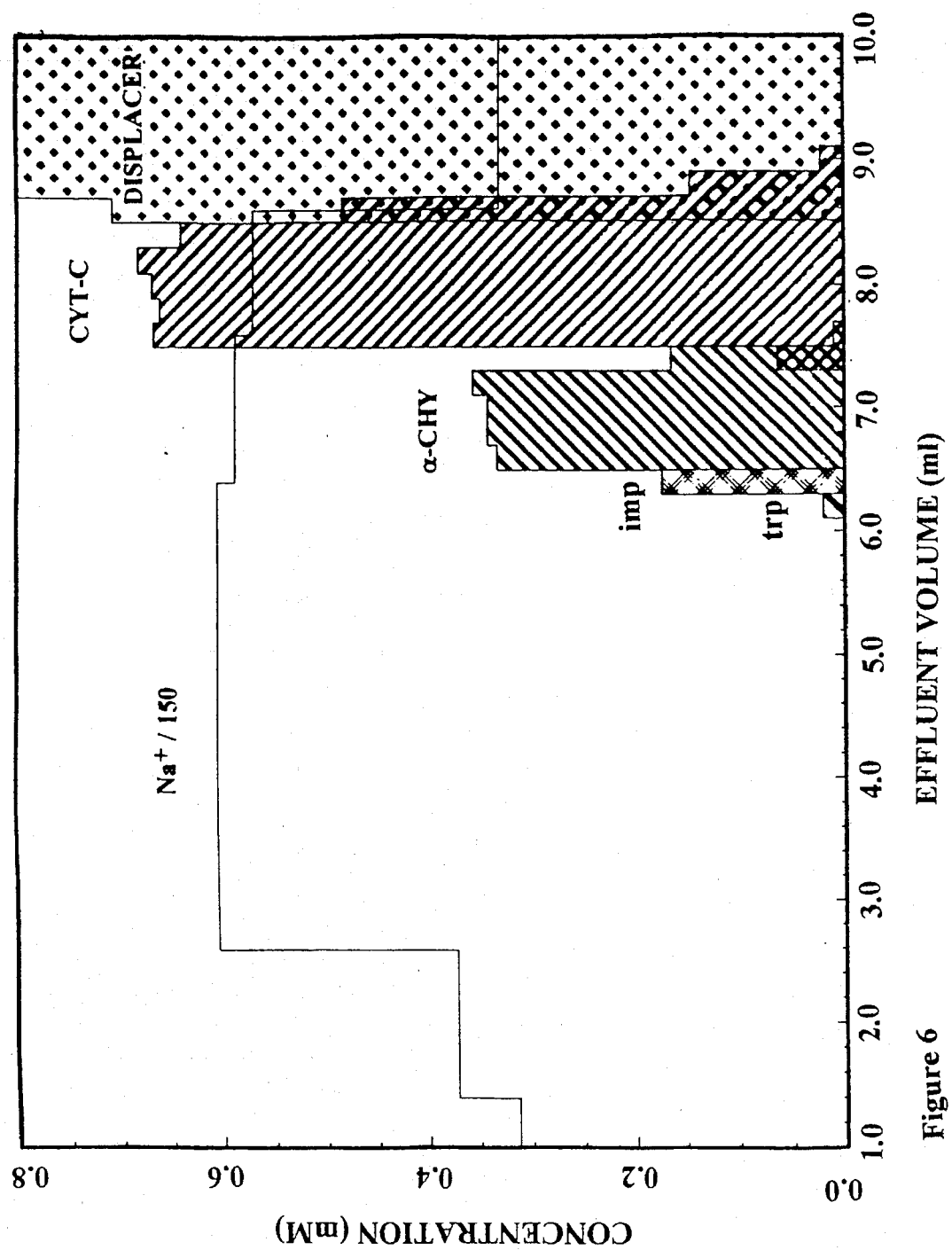
FIGS. 6, 7 and 8 are chromatograms of proteins using displacers of the invention.

The results of the displacement chromatography of the two-protein mixture of α-chymotrypsinogen A and cytochrome-C with the zero generation dendritic displacer are shown in FIG. 6. As seen in the figure, an excellent displacement separation of the two proteins is observed in highly concentrated adjacent zones with sharp boundaries and relatively minimal mixing. This result is truly revolutionary, and is of profound significance for implementation of displacement chromatography for large-scale protein separations.

It is seen that the zero, first and second generation dendritic polyelectrolytes function as efficient displacers of proteins in ion-exchange systems. More significantly the ability of a low molecular weight compound such as the 'zero' generation dendrimer (M.W. 480) to displace relatively high molecular weight proteins is quite exciting in the current context of understanding displacement phenomena. Since the molecular weight and number of charged groups on the dendrimers appear to have little effect on their efficacy as displacers, it may be more advantageous to use a 'zero' generation dendrimer as a displacer. The synthesis of these molecules is much easier and involves fewer steps; (hence they are cheaper). They have the additional advantage of easy separation from any feed component zones during post-displacement, size-based downstream processing.

Other low molecular weight electrolytes also appear to function effectively as displacers for proteins. For example, modified amino acids and charge-bearing antibiotics can be used as displacers. By modified it is meant that the amino acid is altered so as to change it from amphoteric to either cationic (for cation exchange displacement chromatography) or anionic (for anion exchange chromatography). This is most conveniently accomplished by esterifying the carboxylate to produce cationic species or acylating the amine to produce anionic species.

Displacers whose charge is derived from carboxylate tend not to be very effective anionic displacers because of their lower characteristic charge at a pH commonly used in chromatography; as a result, they would have to have an extremely high equilibrium constant to fall counterclockwise from most proteins of interest on the affinity plot. For this reason, among amino acids, acylated taurine derivatives are more likely candidates for anionic displacers.

Figure 7:
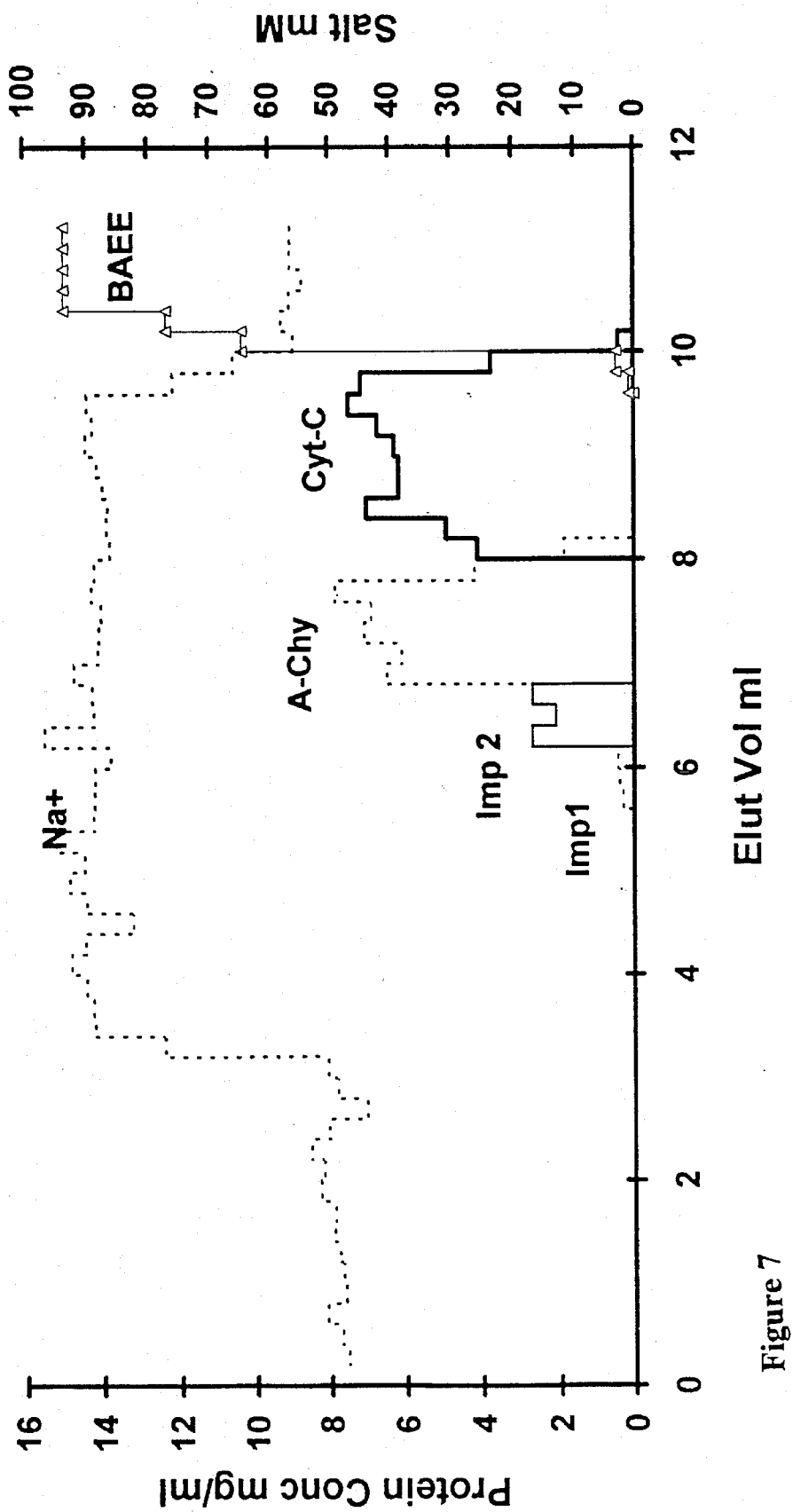

Carboxyl-derivatized amino acids provide very effective cationic displacers. For example, carbobenzoxylysine methyl ester, benzoylarginine ethyl ester (BAEE) and arginine methyl ester are all effective displacers in the displacement chromatography of α-chymotrypsinogen and cytochrome-C. The first two have a single, positive charge; arginine methyl ester has two positive charges, and as a result, a higher affinity for the stationary phase. The resolution of α-chymotrypsinogen and cytochrome-C in isotacic displacement is comparable to the resolution obtained using high molecular weight displacers such as DEAE dextran. An example of a displacement chromatogram of α-chymotrypsinogen A and cytochrome C on an 8 micron strong cation exchange column using 45 mM benzoyl arginine ethyl ester in a 50 mM salt solution at pH 6.0 is shown in FIG. 7. The modified amino acid displacers can be purchased in a very pure form at a cost which is a small fraction of the cost of high molecular weight displacers. In addition, their small size provides them with better transport properties and faster kinetics.

Figure 8:
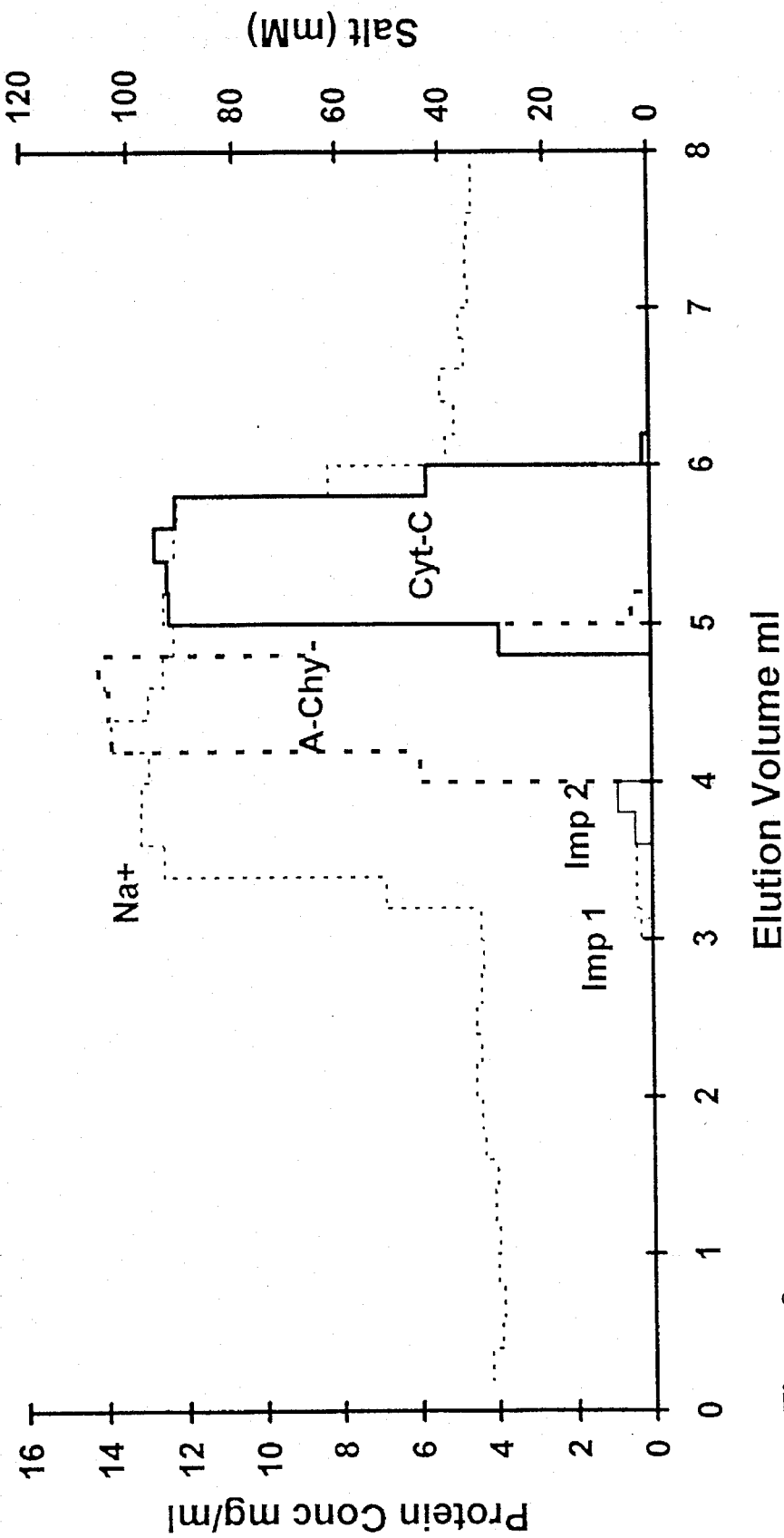

Many antibiotics have the virtue that they are small enough to be removed easily if found in desired protein fractions, but in addition, they can often be advantageously left in the protein fraction. In order to achieve the desired combination of high characteristic charge and equilibrium constant, it appears that antibiotics having one or more strongly dissociating functionalities are particularly useful. Such antibiotics include the streptomycins, which have two guanidine functionalities. An example of a displacement chromatogram of α-chymotrypsinogen A and cytochrome C on an 8 micron strong cation exchange column using 45 mM streptomycin sulfate (m.w. 581) in a 30 mM salt solution at pH 6.0 is shown in FIG. 8.

The demonstration that aminoacid esters, dissociated antibiotics and zero generation dendrimers, all having molecular weights under 600, are highly effective displacers confirms that molecular weights above 2000 are not necessary for displacers for protein chromatography. Indeed we have found no instance of a charged species of molecular weight below 2000 that did not work, as long as the characteristic charge and equilibrium constant were such that the SMA analysis (shown in FIG. 5 and explained above) predicted efficacy.

A displacement separation of a two-component protein mixture was also carried out using crude PETMA (12) as the displacer in a 100×5 mm cation-exchange column. Although the protein components were displaced and well separated in adjacent zones, the effluent profile exhibited similar characteristics to earlier displacements with impure DEAE-dextran displacers. Most strikingly, the cytochrome-C zone was considerably less concentrated in relation to the α-chymotrypsinogen A zone. Apparently, impurities in the displacer contributed to the desorption of the proteins and depression of their isotherms. It is therefore believed advantageous to purify the dendrimers.

One characteristic of dendrimers is that a variety of terminal moieties may reside on the surface of the dendrimer. The terminal groups can be readily converted to functionalities that provide the potential for different utilities, and dendrimers possess a very high density of these terminal moieties which reside in the final exterior layer. When the organic groups on the surface of these compact molecules are functionalized to be charged groups, such as quaternary ammonium salts and sulfonates, they exhibit higher affinity toward chromatographic media than some proteins, making them useful as a new type of displacer in chromatographic separation. The synthesis of the backbone of a dendritic polyether is shown in Scheme 1 and its functionalization pathway to novel poly(ether-amine)s is illustrated in Scheme 2. The functionalization of dendrimeric precursors to provide anionic dendrimers (sulfonates) is shown in Scheme 3. The strategy used in Scheme 1 is a modified procedure derived from the work of Hall and Padias [*J. Org. Chem.* 52, 5305 (1987)]. Pentaerythritol (PE) is also the initiator core but 1-methyl-4-(hydroxymethyl)-2, 6,7-trioxabicyclo-[2.2.2]-octane (MHTBO) is used as the building block instead of the hydroxymethyl bicyclic orthoformate (HTBO). N,N-dimethylethanolamine is used as the synthon to introduce tertiary amine sites.

SCHEME 1

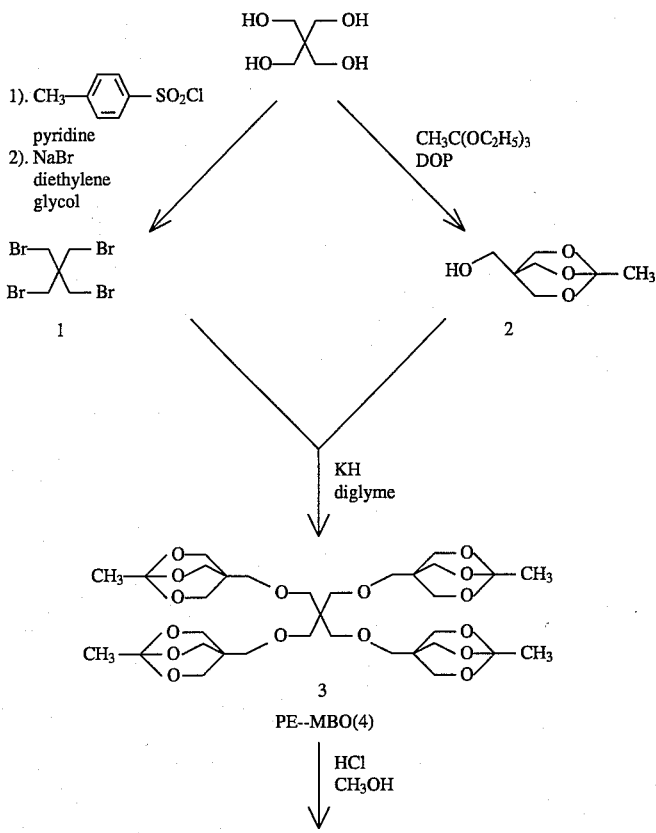

-continued
SCHEME 1
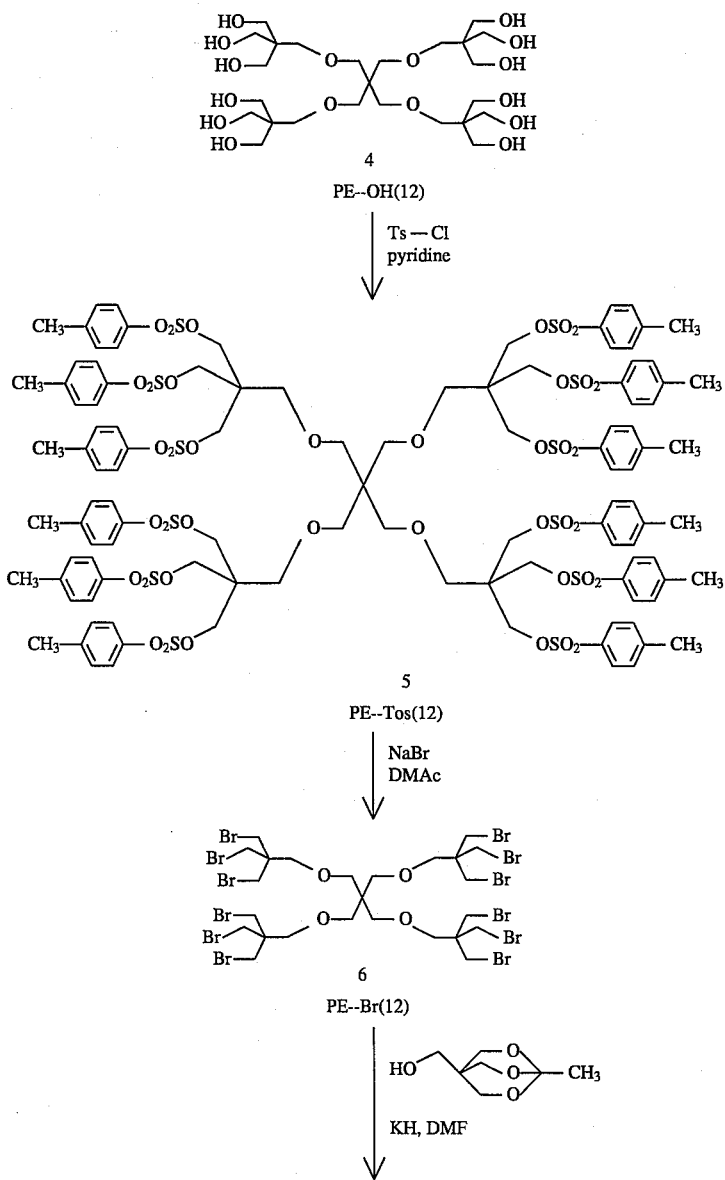

-continued
SCHEME 1
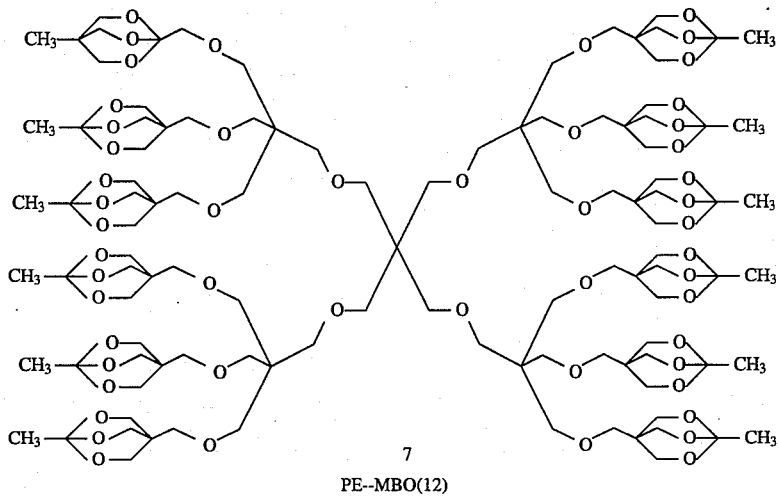
7
PE—MBO(12)
↓ HCl
CH3OH
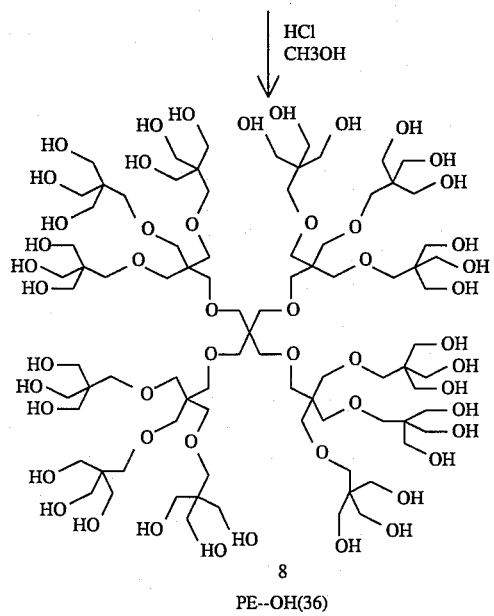
8
PE—OH(36)
Ts—Cl
pyridine -continued
SCHEME 1
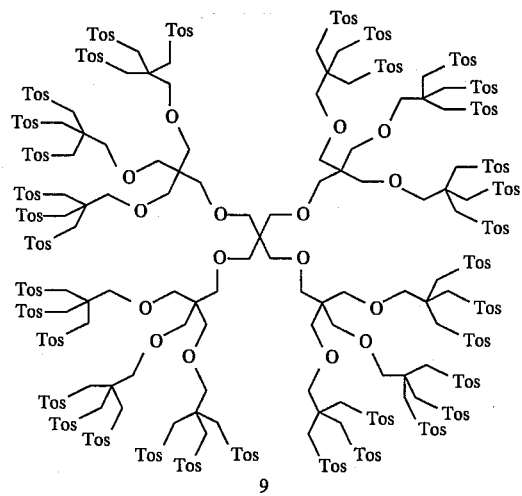
9
PE—Tos(36)
| NaBr
| DMAc
↓
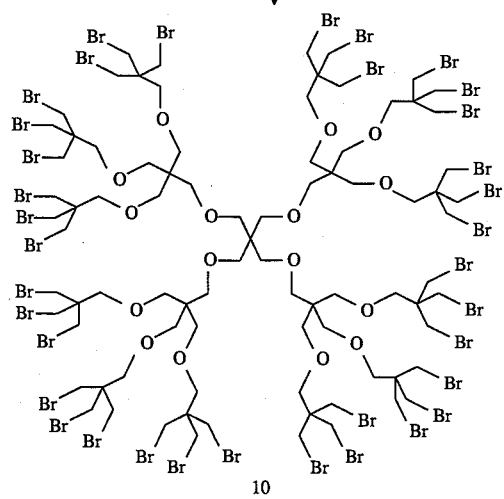
10
PE—Br(36)

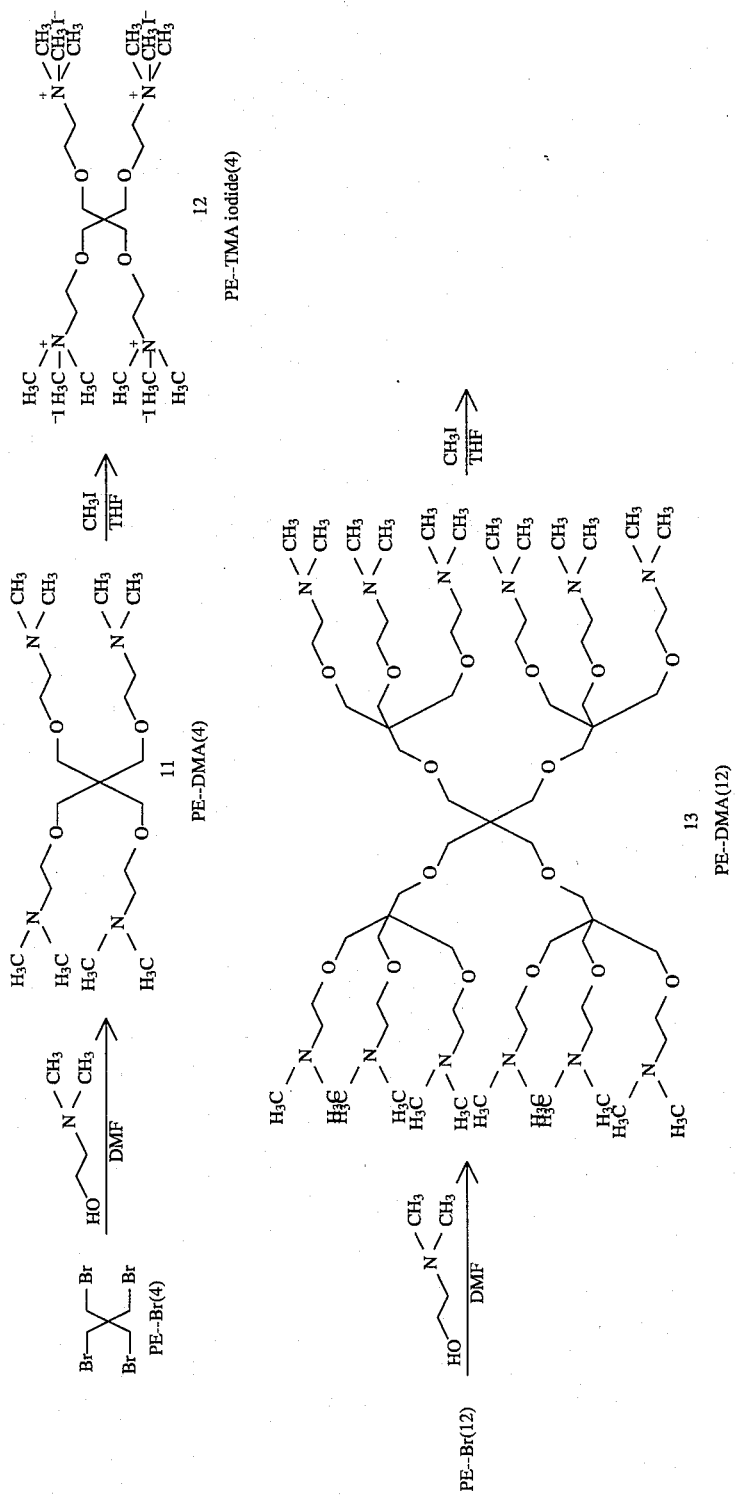

-continued
SCHEME 2
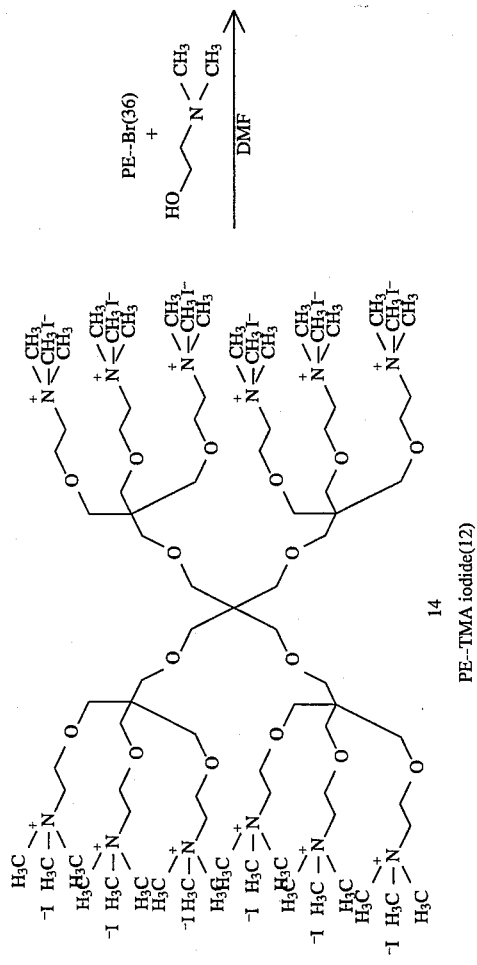
PE—TMA iodide(12)

-continued
SCHEME 2
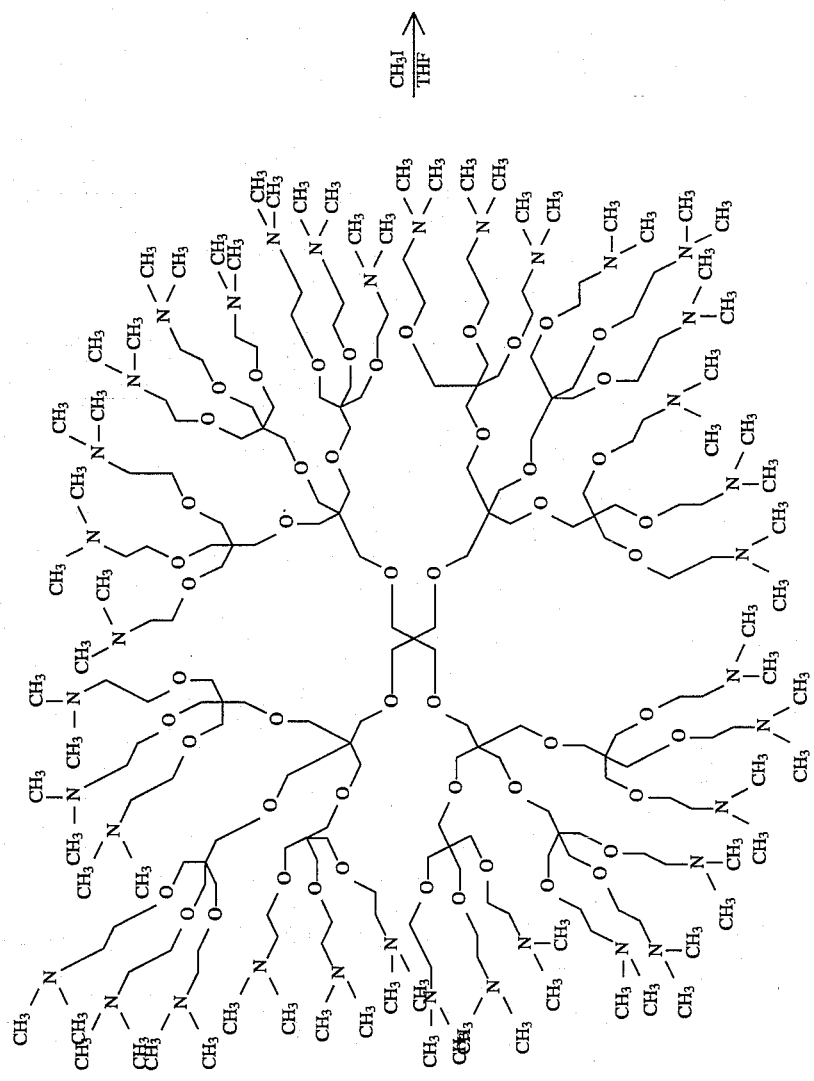
PE-DMA(36)

-continued
SCHEME 2
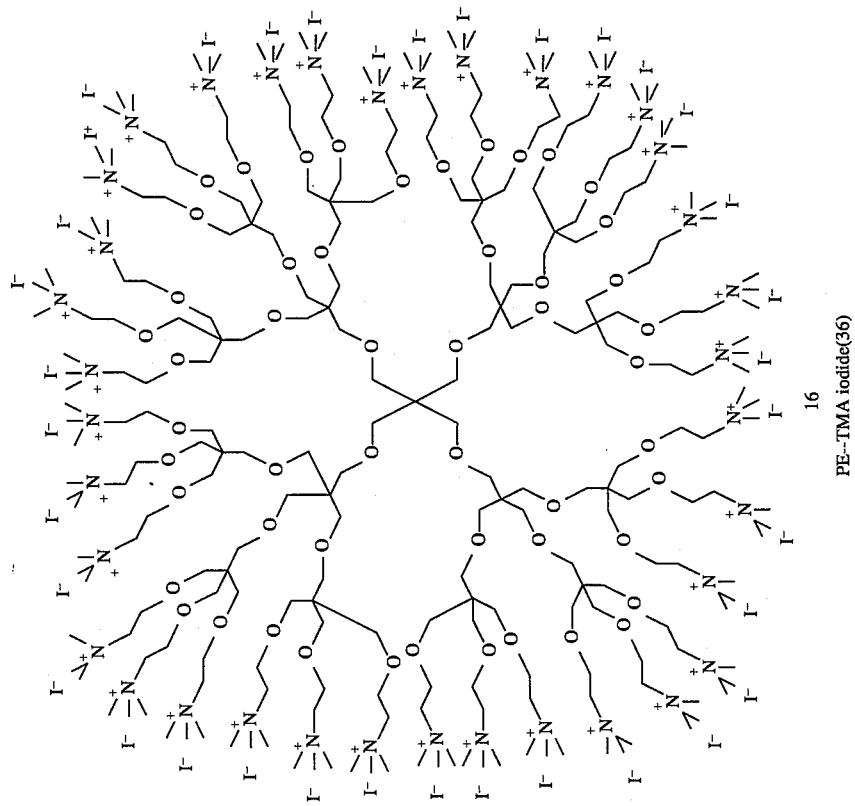
PE—TMA iodide(36)

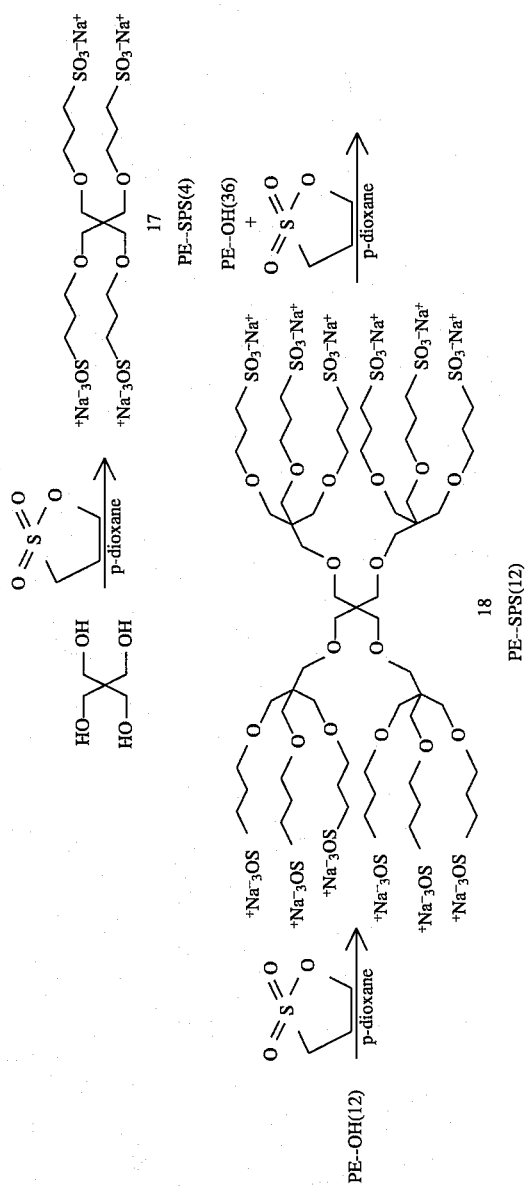

-continued
SCHEME 3
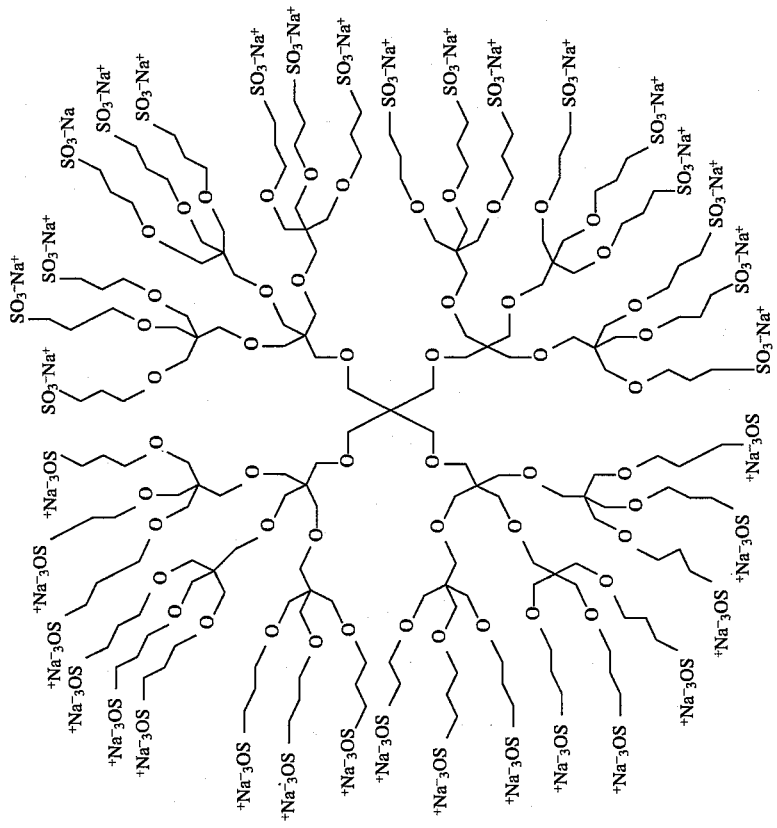
PE—SPS(36)
19

Preparation of Dendrimeric Electrolytes

Hexane, tetrahydrofuran (THF), and 2-methoxyethyl ether (diglyme) were dried over sodium and distilled right before use. N,N-dimethylformamide (DMF) was purchased from Aldrich Chemical Co. in HPLC grade, All other solvents and reagents were used without additional purification unless specified in the procedure.

Pentaerythrityl Tetrabromide, PE-Br(4) (compound 1)

In a 1 L, three-necked, round-bottom flask equipped with a mechanical stirrer and a thermometer were placed pentaerythritol (26.0 g. 0.19 mol) and 200 mL of pyridine. Stirring was initiated and to the suspension, cooled in an ice-bath, was added p-toluenesulfonyl chloride (152.52 g, 0.8 mol) as a solid at such a rate that the temperature did not rise above 30° C. After the addition was completed the resulting slurry was stirred at 35°–40° C. for another two hours. The slurry was then added slowly to a vigorously stirred solution of 200 mL of water, 400 mL of methanol and 160 mL of concentrated hydrochloric acid. The crude white pentaerythrityl toluenesulfonate was further cooled by adding more ice, filtered with suction and washed with 1 L of water and 200 mL of cold methanol in two portions.

In a 1 L, three-necked, round-bottom flask fitted with a mechanical stirrer, a thermometer and a condenser were mixed the slightly wet pentaerythrityl toluenesulfonate (about 140 g), sodium bromide (120 g, 1.16 mol) and 300 mL of diethylene glycol. The mixture was then heated to 140°–150° C. with slow stirring and reacted in this temperature range overnight. After being cooled to about room temperature, the mixture was poured into 400 mL of water with stirring, the precipitate was filtered with suction and washed with 500 mL of water. The crude product was dried under vacuum (1 torr) at 50° C. overnight and recrystallized from acetone. Yield: 52g (70%). Mp: 157°–160° C.

1-Methyl-4-(hydroxymethyl)-2,6,7-trioxabicyclo [2.2.2]octane (MHTBO, compound 2)

Pentaerythritol (13.6 g, 0.1 mol), triethyl orthoacetate (16.22 g, 0.1 mol, 18.3 mL), pyridine p-toluenesulfonate (PPTS) (0.5 g, 2 mmol) and 100 mL of dioctyl phthalate were mixed in a 250 mL, round-bottom flask fitted with a regular distillation apparatus. The mixture was heated to 130°–140° C. and ethanol was slowly distilled. When the amount of ethanol was close to the theoretical value the pressure was reduced to <0.1 torr and the product was distilled in vacuo. The white product which distilled crystallized in the condenser to give 13.6– 14.9 g of MHTBO. Yield: 85–93%. The compound can be recrystallized from toluene but can be used directly. Mp: 110°–112° C.

PE-MBO (4) (compound 3)

In a 500 mL, three-necked flask equipped with a mechanical stirrer, a thermometer and an addition funnel, under an argon atmosphere, potassium hydride (2.8 g, 0.07 mol, 8.0 g of 35% suspension) was washed twice with hexane, the washings were decanted, and 100 mL of diglyme was added. After the mixture was cooled to 0° C. with stirring, a solution of 10.25 g (0.064 mol) of MHTBO in 100 mL of diglyme was added dropwise and the mixture was stirred at room temperature for three hours. Then a solution of 5.82 g (0.015 mol) of pentaerythrityl tetrabromide in 100 mL of diglyme was added dropwise also at room temperature. The mixture was heated to reflux for 24 hours. The mixture was then poured into 600 mL of ice water and the precipitate was filtered, washed with water, and dried under vacuum (1 torr) at 50° C. overnight. A white solid (8.2 g, 78%) was obtained. The Beilstein test for bromide was negative. The product was finally recrystallized from 4:1 ethyl acetate/hexane. Yield: 5.86 g, 55%. Mp: 220° C. slight shrinkage, 230°–244° C. melting.

PE-OH (12) (compound 4)

In a 250 mL, round-bottom flask PE-MBO(4) (6.0 g, 8.53 mmol) was mixed with 100 mL of methanol and 1 mL of concentrated HCl. The mixture was heated slowly to reflux and kept under reflux for one hour. Methanol and methyl acetate were distilled off until only about ⅓ of the solvent remained. The white product was filtered and dried. Yield: 4.86 g (8.0 mmol), 94%. Mp: 180° C. with shrinkage, 220°–235° C. melting.

PE-Tos(12) (compound 5)

In a 500 mL Erlenmeyer flask PE-OH(12) (2.24 g 3.68 mmol) was dissolved in 40 mL of pyridine and cooled to 0° C. A solution of 21.2 g of p-toluenesulfonyl chloride (0.11 mol, 30 equiv) in 100 mL of pyridine was added dropwise through an addition funnel. The solution was stirred for another hour at 0° C. and then left at room temperature for four days. The mixture was poured into 500 mL of ice water and the solvent was decanted after the precipitate agglomerated at the bottom of the beaker. The crude product, 9 g, was dried under vacuum (1 torr) at 50° C. overnight and was then recrystallized from 4:1 ethanol/chloroform. Yield: 8.16 g (3.32 mmol), 90%. Mp: 130°–133° C.

PE-Br (12) (compound 6)

PE-Tos (12) (8.0 g, 3.25 mmol) was dissolved in 50 mL of N,N-dimethylacetamide (DMAc) and 10.06 g of NaBr (98 mmol, 30 equiv) was then added. The resulting suspension was stirred and heated to 150° C. and kept at this temperature for another hour. The mixture was cooled to room temperature and poured into ice water. The precipitate was filtered, dried under vacuum (1 torr) overnight and recrystallized from ethyl acetate. Yield: 3.40 g (77%). Mp: 150° C. with shrinkage, 172°–177° C. melting.

PE-MBO(12) (compound 7)

In a 500 mL, three-necked, round-bottom flask fitted with a mechanical stirrer, a thermometer and an addition funnel under an argon atmosphere potassium hydride (1.6 g, 40 mmol, 4.57 g of 35% suspension) was washed with hexane twice, the washes were decanted and 100 mL of DMF was added. The mixture was cooled to 0° C. and a solution of 5.76 g of MHTBO (compound 2) (36 mmol, 24 equiv) in 50 mL of DMF was added dropwise. The resulting suspension was stirred for three hours at room temperature. The dodecabromide (2.05 g, 1.5 mmol) was dissolved in 100 mL of DMF at 50° C. and then was added rapidly dropwise to the reaction flask immediately while still warm. The mixture was heated to reflux for 24 hours and then poured into ice water containing about 50 g of sodium chloride. The precipitate was filtered and dried under vacuum (1 torr) at 40° C., overnight. The crude yield was quantitative (3.45 g) and the product was purified by column chromatography with silica gel as the stationary phase and a mixture of 1:1 ethyl acetate/hexane as the eluent. $R_f$ value: 0.42. Yield: 2.9 g (1.25 mmol), 82%. The Beilstein test for halogen was negative. Mp: 78° C. with shrinkage, 88°–90° C. gelation, 170° C. softening.

PE-OH (36) (compound 8)

In a 250 mL, round bottom flask were placed PE-MBO(12) (4.4 g, 1.9 mmol), 100 mL of methanol and 1 mL of concentrated HCl. The mixture was heated to reflux for one hour. Methanol and methyl acetate were distilled until only 15–20 mL of the solution remained and the solution was transferred to a beaker. After the rest of the solvent was evaporated completely, the syrup was dried under vacuum (1 torr) to yield a foam. Yield: 3.35 g (1.66 mmol), 88%. Mp: 75° C. with shrinkage, 83°–85° C. gelation, 220°–230° C. softening.

PE-Tos (36) (compound 9)

In a 500 mL Erlenmeyer flask PE-OH(36) (4.17 g, 2.05 mmol) was dissolved in 180 mL of pyridine and cooled to 0° C. A solution of p-toluenesulfonyl chloride (29.4 g, 0.15 mol, 75 equiv) in 200 mL of pyridine was added dropwise. The mixture was stirred for another hour at 0° C. and then left at room temperature for 7 days. The brown solution was poured into 2 L of ice water and the precipitate was filtered and dried under vacuum (1 torr) at 40° C. overnight. Yield: 14.36 g (1.88 mol), 92%. Mp: 120° C. with shrinkage, 220°–245° C. melting.

PE-Br (36) (compound 10)

In a 250 mL, three-necked, round bottom flask were mixed 7.58 g (1.0 mmol) of PE-Tos(36), 8.32 g (80 mmol, 80 equiv) of NaBr and 100 mL of DMAc. The mixture was stirred and heated to 150° C. and kept at this temperature for one hour. Then the mixture was cooled to room temperature and poured into 2 L of ice water with stirring. The precipitate was filtered, washed with another 500 mL of water and dried under vacuum (1 torr) at room temperature overnight. Yield: 4.18 g, 98%. Mp: 48° C. with shrinkage. 52°–68° C. melting.

Tetrakis [((N,N dimethylamino)ethoxy)methyl]methane, PE-DMA (4) (compound 11)

In a 500 mL, three necked, round-bottom flask equipped with a mechanical stirrer, an addition funnel and a thermometer, potassium hydride (5.2 g, 0.13 mol, 14.8 g of a 35% suspension) was washed with hexane twice under an argon atmosphere and 100 mL of DMF was added. When the mixture was cooled to 0° C. a solution of 10.7 g (0.12 mol, 6 equiv) of N,N-dimethylethanolamine in 100 mL of DMF was added dropwise and stirred at room temperature for three hours. A solution of 7.8 g (0.02 mol) of pentaerythrityl tetrabromide in 100 mL of DMF was added dropwise. The mixture was heated to 80° C. and reacted at 80°–90 C. for 12 hours. Then the temperature was raised to reflux for another 12 hours. The resulting mixture was cooled to below 50° C. and poured into 300 mL of ice water. All of the solvents were removed on a rotavapor and the residue was extracted with 800 mL of ethyl ether in a few portions, and the combined extracts were dried over $MgSO_4$. After the ether was evaporated, the crude product was distilled under vacuum (<0.1 torr) to obtain 5.7 g of oily liquid PE-DMA(4). The compound was further purified to a clear liquid on an $Al_2O_3$ column using a mixture of 4:1 ethyl acetate/hexane as the eluent. $R_f$ value: 0.57. Yield: 4.66 g 59%. Bp: 140°–143° C. (0.03 mmHg).

Tetrakis [((N,N,N-trimethylammonium iodide) ethoxy)methyl]methane, PE-TMA iodide (4) (compound 12)

In a 100 mL, three necked flask were placed PE-DMA(4) (2.3 g, 5.5 mmol) and 30 mL of THF under an argon atmosphere. The solution was cooled to 0° C. and a solution of $CH_3I$ (9.3 g, 66 mmol, 12 equiv, 4.1 mL) in 20 mL of THF was added dropwise. After the addition was completed the mixture was stirred at room temperature for five more hours. The yellowish precipitate was filtered, dried under vacuum (1 torr) at 60° C. overnight and finally recrystallized from methanol. The compound is highly hygroscopic. Yield: 3.84 g, 70%.

PE-DMA(12) (compound 13)

The procedure is similar to the one used for PE-DMA(4). Potassium hydride (2.8 g, 0.07 mol, 8.0 g of a 35% suspension) was washed with hexane twice under an argon atmosphere and 100 mL of DMF was added. A solution of 6 mL (0.06 mol, 5.34 g) of N,N-dimethylethanolamine in 50 mL of DMF was added dropwise at 0° C. and the mixture was stirred at room temperature for three hours. PE-Br(12) (2.72g, 32 mmol) was dissolved in 150 mL of DMF at 50° C. and the solution was added while still warm through an addition funnel, dropwise. The mixture was heated to reflux for 24 hours and poured into 300 mL of ice water. After all the DMF and water were evaporated, the residue was extracted with 800 mL of ether in several portions and dried over $MgSO_4$. The ether solution was filtered and concentrated to about 200 mL. In a 300 mL, three necked flask, HCl gas was introduced to the solution and the solvent was decanted when no more salt was formed. The salt was washed with anhydrous ether twice, dried under argon for half an hour, dissolved in water and basified to pH>10. The resulting aqueous solution was dried on a rotavapor and the residue was extracted with 500 mL of ether and dried over $MgSO_4$. After the ether was evaporated, 2.1 g of fairly pure product was obtained. The compound is a viscous oil; bp 220° C. at 0.02 torr. Yield: 72%.

PE-TMA iodide (12) (compound 14)

The procedure is identical with the one used for PE-TMA (iodide(4). PE-DMA (12) (2.04 g 1.4 mmol) was dissolved in 60 mL of THF. At 0° C. a solution of 3.2 mL (7.12 g, 50 mmol, 36 equiv.) of $CH_3I$ in 20 mL THF was added dropwise. The mixture was stirred at room temperature for another three hours. The yellow precipitate was filtered and dried under vacuum (1 torr) at 60° C. overnight. This salt cannot be recrystallized from methanol and was further purified by ultrafiltration before being tested as a displacer. Yield: 3.74 g, 84%.

PE-DMA(36) (compound 15)

This procedure is identical with the one used for PE-DMA(12). Potassium hydride (2.8 g, 0.07 mmol, 8.0 g of 35% suspension) was washed twice with hexane and 100 mL of DMF was added. At 0° C. a solution of 6.4 mL (5.7 g, 64 mmol, 80 equiv.) of N,N-dimethylethanolamine in 50 mL of DMF was added and the mixture was stirred at room temperature for three hours. PE-Br(36) (3,43 g, 0.8 mmol) was dissolved in 100 mL of DMF and added dropwise at room temperature. The mixture was then heated to reflux for 24 hours and poured into 200 mL of ice water. After all solvents were removed, the residue was extracted with 800 mL of ether. The polyamine was converted to a salt by bubbling HCl gas into an ether solution and then was freed by basifying the aqueous solution to pH>10. This compound is a very viscous syrup and is highly hygroscopic. Yield: 1.86 g, 51%.

PE-TMA iodide (3 6) (compound 16)

The procedure is also identical to the one used for PE-TMA iodide(4) and PE-TMA(12). PE-DMA(36) (1.79 g, 0.39 mmol) was dissolved in 100 mL of THF and cooled to 0° C. A solution of 4.2 g (1.82 mL, 30 mmol, 75 equiv.) of $CH_3I$ in 20 mL of THF was added and the mixture was stirred at room temperature for another three hours. The precipitate was then filtered and dried under vacuum (1 torr) at 60° C. overnight. Yield: 2.8 g, 75%.

While the invention has been particularly shown and described with reference to preferred embodiments thereof, it will be understood by those skilled in the art that other changes in form and details may be made therein without departing from the spirit and scope of the invention.

We claim:

1. A method for purifying a protein comprising loading said protein in a suitable loading solvent onto an ion exchange stationary phase and displacing said protein from said stationary phase by displacement chromatography using a cationic displacer of molecular weight less than 1620.

2. A method according to claim 1 wherein said displacer is a poly(quaternary ammonium) salt.

3. A method according to claim 1 wherein said displacer is

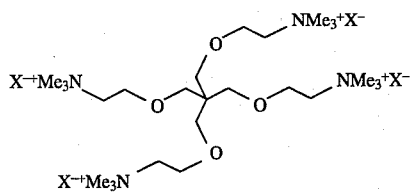

wherein $X^-$ is a counter anion selected from the group consisting of halogen, sulfate, sulfonate, perchlorate, acetate, phosphate and nitrate.

4. A method according to claim 1 wherein said displacer is selected from the group consisting of aminoacid esters, N-acylaminoacids, peptide esters and N-acyl peptides.

5. A method according to claim 4 wherein said displacer is selected from the group consisting of lower alkyl esters of lysine, lower alkyl esters of arginine, lower alkyl esters of $N^\alpha$-acylated lysine and lower alkyl esters of $N^\alpha$-acylated arginine.

6. A method according to claim 1 wherein said displacer is a dendritic polymer.

7. A method according to claim 1 wherein said displacer is a cationic antibiotic.

8. A method according to claim 1 wherein said displacer is dissolved in a solvent system and said displacer is selected from electrolytes whose characteristic charge (ν) and equilibrium constant (K) are such that when a coordinate system representing logK on the ordinate and ν on the abscissa is created, a line constructed from a point A on the ordinate axis through a point defined by the K and the ν of the displacer has a greater slope than a corresponding line constructed from the same point A through a point defined by the K and the ν of the protein to be purified, said point A corresponding in value to the slope of the displacer operating line (Δ) in said solvent system in which said displacer is dissolved.

9. A method for purifying a protein comprising loading said protein in a suitable loading solvent onto an ion exchange stationary phase and displacing said protein from said stationary phase by displacement chromatography using a dendritic polyelectrolyte displacer.

10. A method according to claim 9 wherein said stationary phase is a cation exchange resin and said polyelectrolyte displacer is a polycation.

11. A method according to claim 10 wherein said polyelectrolyte displacer is a poly(quaternary ammonium) salt.

12. A method according to claim 11 wherein said displacer is

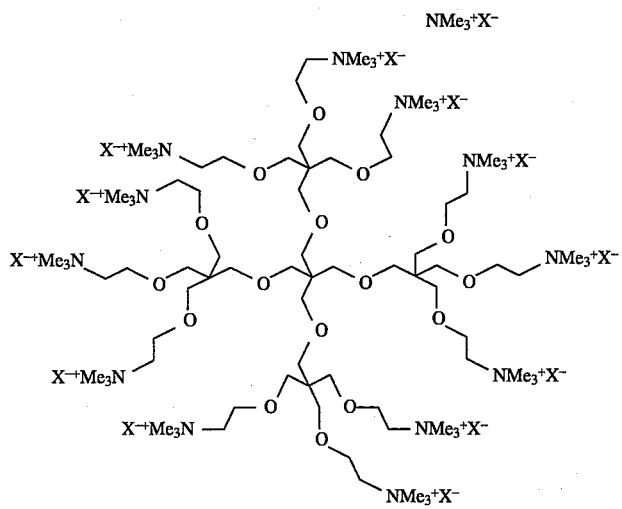

wherein $X^-$ is a counter anion selected from the group consisting of halogen, sulfate, sulfonate, perchlorate, acetate, phosphate and nitrate.

13. A compound of formula

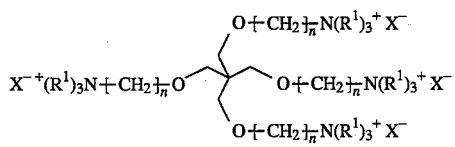

wherein $R^1$ is lower alkyl, n is 2 to 6, and X is halogen, sulfate, sulfonate, perchlorate, acetate, phosphate or nitrate.

14. A compound of formula

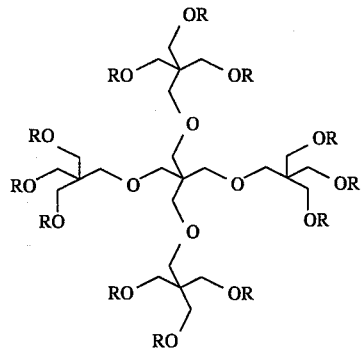

wherein R is $-(CH_2)_n-N(R^1)_3{}^+X^-$, $R^1$ is lower alkyl, n is 2 to 6, and X is halogen, sulfate, sulfonate, perchlorate, acetate, phosphate or nitrate.

* * * * *